United States Patent
Reisner et al.

(10) Patent No.: US 11,179,448 B2
(45) Date of Patent: *Nov. 23, 2021

(54) GENETICALLY MODIFIED ANTI-THIRD PARTY CENTRAL MEMORY T CELLS AND USE OF SAME IN IMMUNOTHERAPY

(71) Applicant: Yeda Research and Development Co. Ltd., Rehovot (IL)

(72) Inventors: Yair Reisner, Old Jaffa (IL); Noga Or-Geva, Rehovot (IL); Eran Ophir, Rehovot (IL); Yaki Eidelstein, Rehovot (IL); Rotem Gidron Budovsky, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/744,905

(22) PCT Filed: Jul. 14, 2016

(86) PCT No.: PCT/IL2016/050775
§ 371 (c)(1),
(2) Date: Jan. 15, 2018

(87) PCT Pub. No.: WO2017/009853
PCT Pub. Date: Jan. 19, 2017

(65) Prior Publication Data
US 2018/0207272 A1    Jul. 26, 2018

Related U.S. Application Data

(60) Provisional application No. 62/193,229, filed on Jul. 16, 2015, provisional application No. 62/193,207, filed on Jul. 16, 2015.

(51) Int. Cl.
| | |
|---|---|
| *A61K 39/00* | (2006.01) |
| *A61K 35/17* | (2015.01) |
| *C12N 5/078* | (2010.01) |
| *C12N 5/0783* | (2010.01) |
| *A61P 31/00* | (2006.01) |
| *A61P 35/04* | (2006.01) |
| *A61K 39/395* | (2006.01) |
| *C07K 16/28* | (2006.01) |
| *A61K 35/12* | (2015.01) |

(52) U.S. Cl.
CPC ............ *A61K 39/001* (2013.01); *A61K 35/17* (2013.01); *A61K 39/39566* (2013.01); *A61P 31/00* (2018.01); *A61P 35/04* (2018.01); *C07K 16/2896* (2013.01); *C12N 5/0636* (2013.01); *C12N 5/0637* (2013.01); *C12N 5/0648* (2013.01); *A61K 2035/122* (2013.01); *A61K 2039/5158* (2013.01); *C12N 2501/2307* (2013.01); *C12N 2501/2315* (2013.01); *C12N 2501/2321* (2013.01); *Y02A 50/30* (2018.01)

(58) Field of Classification Search
CPC .......... A61K 39/001; A61K 2039/5158; A61K 39/39566; A61K 35/17; A61K 2035/122; A61P 31/00; A61P 35/04; C07K 16/2896; Y02A 50/30; C12N 2501/2315; C12N 2501/2321; C12N 5/0648; C12N 5/0637; C12N 5/0636; C12N 2501/2307
See application file for complete search history.

(56) References Cited

U.S. PATENT DOCUMENTS

| | | | |
|---|---|---|---|
| 6,447,765 B1 | 9/2002 | Horwitz | |
| 6,759,035 B2 | 7/2004 | Horwitz | |
| 6,803,036 B1 | 10/2004 | Horwitz | |
| 7,270,810 B2 | 9/2007 | Reisner et al. | |
| 8,974,779 B2 | 3/2015 | Reisner et al. | |
| 9,421,228 B2 * | 8/2016 | Reisner | A61K 39/001 |
| 9,738,872 B2 * | 8/2017 | Reisner | A61K 39/001 |
| 9,833,482 B2 | 12/2017 | Reisner et al. | |
| 9,987,354 B2 | 6/2018 | Fraser et al. | |
| 9,993,548 B2 | 6/2018 | Maldonado | |
| 10,039,822 B2 | 8/2018 | Altreuter et al. | |
| 10,155,818 B2 | 12/2018 | Seibert et al. | |
| 10,280,226 B2 | 5/2019 | Seibert et al. | |
| 10,369,172 B2 | 8/2019 | Reisner et al. | |

(Continued)

FOREIGN PATENT DOCUMENTS

| | | |
|---|---|---|
| CN | 103930130 | 7/2014 |
| CN | 104470542 | 3/2015 |

(Continued)

OTHER PUBLICATIONS

Neeson P, Shin A, Tainton KM, Guru P, Prince HM, Harrison SJ, Peinert S, Smyth MJ, Trapani JA, Kershaw MH, Darcy PK, Ritchie DS. Ex vivo culture of chimeric antigen receptor T cells generates functional CD8+ T cells with effector and central memory-like phenotype. Gene Ther. Sep. 2010;17(9):1105-16. Epub Apr. 2, 2010.*

(Continued)

*Primary Examiner* — Rachel B Gill

(57) ABSTRACT

An isolated cell having a central memory T-lymphocyte (Tcm) phenotype, the cell being tolerance-inducing cell and capable of homing to the lymph nodes following transplantation, the cell being transduced to express a cell surface receptor comprising a T cell receptor signaling module is disclosed. Methods of generating same and using same are also disclosed.

15 Claims, 9 Drawing Sheets
(4 of 9 Drawing Sheet(s) Filed in Color)

(56) References Cited

U.S. PATENT DOCUMENTS

| | | | |
|---|---|---|---|
| 10,751,368 | B2 | 8/2020 | Reisner et al. |
| 2002/0182211 | A1 | 12/2002 | Peach et al. |
| 2003/0003083 | A1 | 1/2003 | Reisner et al. |
| 2003/0022836 | A1 | 1/2003 | Larsen et al. |
| 2003/0049235 | A1 | 3/2003 | Reisner |
| 2003/0083246 | A1 | 5/2003 | Cohen et al. |
| 2004/0022787 | A1 | 2/2004 | Cohen et al. |
| 2004/0136972 | A1 | 7/2004 | Reisner et al. |
| 2005/0123539 | A1 | 6/2005 | Rusnak |
| 2005/0214313 | A1 | 9/2005 | Peach et al. |
| 2006/0269973 | A1 | 11/2006 | Yee |
| 2007/0009511 | A1 | 1/2007 | Hagerty et al. |
| 2007/0264274 | A1 | 11/2007 | Reisner et al. |
| 2008/0131415 | A1 | 6/2008 | Riddell et al. |
| 2008/0160022 | A1 | 7/2008 | Larsen et al. |
| 2008/0279817 | A1 | 11/2008 | Skak |
| 2009/0022730 | A1 | 1/2009 | Raulf et al. |
| 2009/0041769 | A1 | 2/2009 | Peach et al. |
| 2009/0041790 | A1 | 2/2009 | Rusnak |
| 2009/0068203 | A1 | 3/2009 | Rusnak |
| 2009/0232774 | A1 | 9/2009 | Reisner |
| 2010/0022627 | A1 | 1/2010 | Scherer |
| 2010/0041602 | A1 | 2/2010 | Hagerty et al. |
| 2010/0049935 | A1 | 2/2010 | Pichumani et al. |
| 2010/0166756 | A1 | 7/2010 | Cohen et al. |
| 2010/0183612 | A1 | 7/2010 | Peach et al. |
| 2010/0255009 | A1 | 10/2010 | Siemionov |
| 2011/0212071 | A1 | 9/2011 | Reisner et al. |
| 2013/0171108 | A1 | 7/2013 | Reisner et al. |
| 2013/0183322 | A1 | 7/2013 | Reisner et al. |
| 2014/0212398 | A1* | 7/2014 | Reisner ............... A61K 39/001 424/93.71 |
| 2014/0271581 | A1* | 9/2014 | Hyde ................. C12N 5/0638 424/93.21 |
| 2014/0314795 | A1 | 10/2014 | Riddell et al. |
| 2016/0354410 | A1* | 12/2016 | Reisner ............... A61K 39/001 |
| 2017/0216356 | A1* | 8/2017 | Eshhar ............... A61K 31/135 |
| 2018/0193384 | A1* | 7/2018 | Reisner ............... A61K 39/001 |
| 2018/0200300 | A1* | 7/2018 | Reisner ............... A61K 35/17 |
| 2018/0207247 | A1* | 7/2018 | Reisner ............... A61K 35/17 |
| 2019/0091266 | A1 | 3/2019 | Reisner et al. |
| 2019/0338247 | A1 | 11/2019 | Reisner et al. |

FOREIGN PATENT DOCUMENTS

| | | |
|---|---|---|
| EP | 2753351 | 3/2013 |
| JP | 2008-521406 | 6/2008 |
| JP | 2013-537187 | 9/2013 |
| JP | 2014-526244 | 7/2014 |
| JP | 2014-510108 | 10/2014 |
| WO | WO 01/49243 | 7/2001 |
| WO | WO 02/43651 | 6/2002 |
| WO | WO 02/102971 | 12/2002 |
| WO | WO 2005/067956 | 7/2005 |
| WO | WO 2005/092380 | 10/2005 |
| WO | WO 2006/041763 | 4/2006 |
| WO | WO 2006/065495 | 6/2006 |
| WO | WO 2007/023491 | 3/2007 |
| WO | WO 2009/053109 | 4/2009 |
| WO | WO 2010/049935 | 5/2010 |
| WO | WO 2011/053223 | 5/2011 |
| WO | WO 2011/140170 | 11/2011 |
| WO | WO 2012/032525 | 3/2012 |
| WO | WO 2012/032526 | 3/2012 |
| WO | WO 2012/129514 | 9/2012 |
| WO | WO 2013/035099 | 3/2013 |
| WO | WO 2014/031687 | 2/2014 |
| WO | WO 2014/039044 | 3/2014 |
| WO | WO 2014/059173 | 4/2014 |
| WO | WO 2014/152177 | 9/2014 |
| WO | WO 2017/009852 | 1/2017 |
| WO | WO 2017/009853 | 1/2017 |
| WO | WO 2017/203520 | 11/2017 |
| WO | WO 2018/134824 | 7/2018 |

OTHER PUBLICATIONS

Terakura S, Yamamoto TN, Gardner RA, Turtle CJ, Jensen MC, Riddell SR. Generation of CD19-chimeric antigen receptor modified CD8+ T cells derived from virus-specific central memory T cells. Blood. Jan. 5, 2012;119(1):72-82. Epub Oct. 26, 2011.*

Figueroa JA, Reidy A, Mirandola L, Trotter K, Suvorava N, Figueroa A, Konala V, Aulakh A, et. al. Chimeric antigen receptor engineering: a right step in the evolution of adoptive cellular immunotherapy. Int Rev Immunol. Mar. 2015;34(2):154-87.*

Marcus A, Waks T, Eshhar Z. Redirected tumor-specific allogeneic T cells for universal treatment of cancer. Blood. Jul. 28, 2011;118 (4):975-83. Epub Jun. 7, 2011.*

Zimring JC. Location, location, location: advancing veto cell therapies. Blood. Feb. 14, 2013;121 (7): 1069-70. doi: 10.1182/blood-2012-12-472654. PMID: 23411733.*

Wu F, Zhang W, Shao H, Bo H, Shen H, Li J, Liu Y, et. al. Human effector T cells derived from central memory cells rather than CD8(+)T cells modified by tumor-specific TCR gene transfer possess superior traits for adoptive immunotherapy. Cancer Lett. Oct. 10, 2013;339(2):195-207. Epub Jun. 18, 2013. (Year: 2013).*

Gattinoni L, Lugli E, Ji Y, Pos Z, Paulos CM, Quigley MF, Almeida JR, Gostick E, Yu Z, Carpenito C, Wang E, Douek DC, Price DA, June CH, Marincola FM, Roederer M, Restifo NP. A human memory T cell subset with stem cell-like properties. Nat Med. Sep. 18, 2011;17(10):1290-7. (Year: 2011).*

Restriction Official Action dated Jan. 7, 2018 From the U.S. Appl. No. 15/744,881. (8 pages).

Examination Report Under Sections 12 & 13 of the Patents Act, 1970 and the Patents Rules, 2003 dated Jan. 10, 2019 From the Government of India, Intellectual Property India, Patents, Designs, Trade Marks, Geographical Indications Re. Application No. 577/MUMNP/2014. (7 Pages).

Notice of Grounds for Rejection dated Nov. 29, 2018 From the Korea Intellectual Property Office Re. Application No. 10-2014-7009267 and Its Translation Into English. (11 Pages).

Requisition by the Examiner dated Jul. 30, 2018 From the Innovation, Science and Economic Development Canada, Canadian Intellectual Property Office Re. Application No. 2,848,121. (5 Pages).

Official Action dated Jun. 19, 2018 From the U.S. Appl. No. 15/242,666. (54 pages).

Carrio et al. "Initial Antigen Encounter Programs CD8+ TCells Competent to Develop into Memory Cells That Are Activated in an Antigen-Free, IL-7 and IL-15-Rich Environment", The Journal of Immunology, 172: 7315-7323, 2004.

Doiron et al. "The Role of T Cells in Peripheral Blood Mononuclear Cells", Human Tissue Sample Blog, pp. 1-4, 2016.

Klinger et al. "Cyclical Expression of L-Selectin (CD62L) by Recirculating T Cells", International Immunology, 21(4): 443-455, Apr. 1, 2009.

Van Leeuwen et al. "Proliferation Requirements of Cytomegalovirus-Specific, Effector-Type Humans CDS+ T Cells", The Journal of Immunology, 169: 5838-5843, 2002.

International Search Report and the Written Opinion dated Apr. 17, 2018 From the International Searching Authority Re. Application No. PCT/IL2018/050071. (17 Pages).

Ersek et al. "Unique Patterns of CD8+ T-Cell-Mediated Organ Damage in the Act-mOVA/OT-I Model of Acute Graft-Versus-Host Disease", Cellular and Molecular Life Sciences, CMLS, XP036053921, 73(20): 3935-3947, Published Online Apr. 30, 2016.

Geva et al. "The Role of Donor-Derived Veto Cells in Nonmyeloablative Haploidentical HSCT", Bone Marrow Transplantation, XP055461528, 50(S2): S14-S20, Jun. 1, 2015. p. 16-17.

Rajawat et al. "Development of an Enhanced VETO Cells for the Generation of Alloantigen-Specific Tolerance", The Journal of Immunology, XP055462318, 196(1 Suppl.): 140.24, May 1, 2016. Abstract.

Rajawat et al. "Induction of Antigen Specific Transplantation Tolerance Using Chimeric Antigen Receptor Type T Cells Engineered to Kill Allospecific T Cells by A Gene Therapy Immunotherapeutic Approach (TRAN2P.968)", The Journal of Immunology, XP055462376, 194(1 Suppl.): 209.8, May 1, 2015. Abstract.

(56) References Cited

OTHER PUBLICATIONS

Official Action dated May 21, 2019 From the U.S. Appl. No. 15/242,666. (34 pages).
Applicant-Initiated Interview Summary dated May 4, 2015 From the U.S. Appl. No. 13/821,255.
Communication Pursuant to Article 94(3) EPC dated Jun. 4, 2014 From the European Patent Office Re. Application No. 09764302.7.
Communication Pursuant to Article 94(3) EPC dated Dec. 14, 2012 From the European Patent Office Re. Application No. 09764302.7.
Communication Pursuant to Article 94(3) EPC dated Oct. 21, 2015 From the European Patent Office Re. Application No. 12769743.1.
Communication Pursuant to Article 94(3) EPC dated Jan. 24, 2014 From the European Patent Office Re. Application No. 11773345.6.
Communication Pursuant to Article 94(3) EPC dated Jan. 26, 2015 From the European Patent Office Re. Application No. 12769743.1.
Communication Pursuant to Article 94(3) EPC dated Jan. 27, 2014 From the European Patent Office Re. Application No. 11773325.3.
Decision on Rejection dated Dec. 2, 2015 From The State Intellectual Property Office of the People's Republic of China Re. Application No. 201180053858.9 and Its Translation Into English.
Examination Report dated Feb. 1, 2017 From the Institute Mexicano de la Propiedad Industrial, IMPI, Direccion Divisional de Patentes Re. Application No. MX/a/2013/002668 and Its Translation Into English. (8 Pages).
Examination Report dated Feb. 2, 2016 From the Intellectual Property Office of Singapore Re. Application No. 11201400513P.
Examination Report dated Oct. 15, 2015 From the Intellectual Property Office of Singapore Issued by the Austrian Patent Office Re. Application No. 201301743-9.
Examination Report dated Sep. 25, 2017 From the Instituto Mexicano de la Propiedad Industrial, IMPI, Direccion Divisional de Patentes Re. Application No. MX/a/2013/002668 and Its Translation Into English. (16 Pages).
Examination Report dated Jul. 28, 2017 From the Australian Government, IP Australia Re. Application No. 2012305931. (3 Pages).
Examination Report dated Mar. 28, 2016 From the Government of India, Patent Office, Intellectual Property Building Re. Application No. 905/MUMNP/2011.
Examination Report dated Jul. 29, 2016 From the Institute Mexicano de la Propiedad Industrial, IMPI, Direccion Divisional de Patentes Re. Application No. MX/a/2013/002668 and Its Translation Into English.
International Preliminary Report on Patentability dated May 12, 2011 From the International Bureau of WIPO Re. Application No. PCT/IL2009/001014.
International Preliminary Report on Patentability dated Mar. 20, 2014 From the International Bureau of WIPO Re. Application No. PCT/IL2012/050354.
International Preliminary Report on Patentability dated Mar. 21, 2013 From the International Bureau of WIPO Re. Application No. PCT/IL2011/000726.
International Preliminary Report on Patentability dated Mar. 21, 2013 From the International Bureau of WIPO Re. Application No. PCT/IL2011/000727.
International Preliminary Report on Patentability dated Jan. 25, 2018 From the International Bureau of WIPO Re. Application No. PCT/IL2016/050774. (7 Pages).
International Preliminary Report on Patentability dated Jan. 25, 2018 From the International Bureau of WIPO Re. Application No. PCT/IL2016/050775. (7 Pages).
International Search Report and the Written Opinion dated Mar. 7, 2012 From the International Searching Authority Re. Application No. PCT/IL2011/000727.
International Search Report and the Written Opinion dated Feb. 16, 2010 From the International Searching Authority Re. Application No. PCT/IL2009/001014.
International Search Report and the Written Opinion dated Oct. 19, 2016 From the International Searching Authority Re. Application No. PCT/IL2016/050774.
International Search Report and the Written Opinion dated Oct. 19, 2016 From the International Searching Authority Re. Application No. PCT/IL2016/050775.
International Search Report and the Written Opinion dated Jun. 27, 2012 From the International Searching Authority Re. Application No. PCT/IL2011/000726.
International Search Report and the Written Opinion dated Jan. 28, 2013 From the International Searching Authority Re. Application No. PCT/IL2012/050354.
Notice Of Allowance dated Apr. 11, 2017 From the U.S. Appl. No. 13/126,472. (34 pages).
Notice of Reason for Rejection dated Jul. 1, 2016 From the Japanese Patent Office Re. Application No. 2014-529143 and Its Translation Into English.
Notice of Reason for Rejection dated Aug. 4, 2015 From the Japanese Patent Office Re. Application No. 2013-527738 and Its Translation Into English.
Notification of Lack of Unity Dated Feb. 21, 2017 From the Federal Service for Intellectual Property, Rospatent, Federal State Budgetary Institution, Federal Institute of industrial Property, Patents and Trademarks of the Russion Federation Re. Application No. 2014110897 and Its Translation Into English. (8 Pages).
Notification of Office Action and Search Report dated Jan. 23, 2015 From the State Intellectual Property Office of the People's Republic of China Re. Application No. 201280054739.X.
Office Action dated Nov. 3, 2016 From the Israel Patent Office Re. Application No. 231397 and Its Translation Into English. (7 Pages).
Office Action dated Oct. 12, 2015 From the Israel Patent Office Re. Application No. 225102 and Its Translation Into English.
Office Action dated May 14, 2014 From the Israel Patent Office Re. Application No. 212587 and Its Translation Into English.
Office Action dated Apr. 15, 2013 From the Israel Patent Office Re. Application No. 212587 and Its Translation Into English.
Office Action dated Mar. 18, 2015 From The State Intellectual Property Office of the People's Republic of China Re. Application No. 201180053858.9 and Its Translation Into English.
Office Action dated Sep. 23, 2015 From the State Intellectual Property Office of the People's Republic of China Re. Application No. 201280054739.X and Its Translation Into English.
Office Action dated Apr. 29, 2014 From The State Intellectual Property Office of the People's Republic of China Re. Application No. 201180053858.9 and Its Translation Into English.
Official Action dated Aug. 1, 2013 From the U.S. Appl. No. 13/126,472.
Official Action dated Jun. 1, 2017 From the U.S. Appl. No. 14/343,053. (27 pages).
Official Action dated Oct. 3, 2016 From the U.S. Appl. No. 13/126,472.
Official Action dated Oct. 7, 2016 From the U.S. Appl. No. 14/343,053.
Official Action dated May 8, 2014 From the U.S. Appl. No. 13/126,472.
Official Action dated Feb. 12, 2016 From the U.S. Appl. No. 14/343,053.
Official Action dated Nov. 19, 2015 From the U.S. Appl. No. 13/126,472.
Official Action dated Dec. 23, 2016 From the U.S. Appl. No. 14/343,053. (17 pages).
Official Action dated Mar. 23, 2015 From the U.S. Appl. No. 13/821,255.
Official Action dated Jul. 24, 2014 From the U.S. Appl. No. 13/821,255.
Patent Examination Report dated Aug. 23, 2016 From the Australian Government, IP Australia Re. Application No. 2012305931.
Restriction Official Action dated Aug. 14, 2014 From the U.S. Appl. No. 13/821,269.
Restriction Official Action dated Oct. 20, 2015 From the U.S. Appl. No. 14/343,053.
Restriction Official Action dated Dec. 22, 2017 From the U.S. Appl. No. 15/242,666. (8 pages).
Search Report and Written Opinion dated Oct. 10, 2014 From the Intellectual Property Office of Singapore Re. Application No. 11201400513P.

(56) References Cited

OTHER PUBLICATIONS

Search Report dated Apr. 29, 2014 From The State Intellectual Property Office of the People's Republic of China Re. Application No. 201180053858.9 and Its Translation Into English.
Translation dated Feb. 8, 2015 of Notification of Office Action and Search Report dated Jan. 23, 2015 From the State Intellectual Property Office of the People's Republic of China Re. Application No. 201280054739.X.
Translation of Office Action dated Dec. 27, 2012 From the State Intellectual Property Office of the People's Republic of China Re. Application No. 200980153053.4.
Translation of Search Report dated Dec. 27, 2012 From the State Intellectual Property Office of the People's Republic of China Re. Application No. 200980153053.4.
Written Opinion and Search Report dated Feb. 28, 2014 From the Intellectual Property Office of Singapore Issued by the Austrian Patent Office Re. Application No. 201301743-9.
Written Opinion dated Jun. 11, 2015 From the Intellectual Property Office of Singapore Re. Application No. 11201400513P.
Written Opinion dated Feb. 17, 2015 From the Intellectual Property Office of Singapore Issued by the Austrian Patent Office Re. Application No. 201301743-9.
Albrecht et al. "IL-21-Treated Naive CD45RA+ CD8+ T Cells Repressant A Reliable Source for Producing Leukemia-Reactive Cytotoxic T Lymphocytes With High Proliferative Potential and Early Differentiation Phenotype", Cancer Immunology, Immunotherapy: CII, XP002689103, 60(2): 235-248, Feb. 2011. Abstract.
Arditti et al. "Eradication of B-CLL by Autologous and Allogeneic Host Nonreactive Anti-Third-Party CTLs", Blood, 105(8): 3365-3371, Apr. 15, 2005.
Aversa et al. "Full Haplotype-Mismatched Hematopoietic Stem-Cell Transplantation: A Phase II Study in Patients With Acute Leukemia at High Risk of Relapse", Journal of Clinical Oncology, 23(15): 3447-3454, May 20, 2005.
Aversa et al. "Successful Engraftment of T-Cell-Depleted Haploidentical 'Three-Loci' Incompatible Transplants in Leukemia Patients by Addition of Recombinant Human Granulocyte Colony-Stimulating Factor-Mobilized Peripheral Blood Progenitor Cells to Bone Marrow Inoculum", Blood, 84(4): 3948-3955, Dec. 1, 1994.
Aversa et al. "Treatment of High-Risk Acute Leukemia With T-Cell-Depleted Stem Cells From Related Donors With One Fully Mismatched HLA Haplotype", The New England Journal of Medicine, 339(17): 1186-1193, Oct. 22, 1998.
Aviner et al. "Large-Scale Preparation of Human Anti-Third-Party Veto Cytotoxic T Lymphocytes Depleted of Graft-Versus-Host Reactivity: A New Source for Graft Facilitating Cells in Bone Marrow Transplantation", Human Immunology, 66(6): 644-652, Jun. 30, 2005.
Bachar-Lustig et al. "Anti-Third-Party Veto CTLs Overcome Rejection of Hematopoietic Allografts: Synergism With Rapamycin and BM Cell Dose", Blood, 102(6): 1943-1950, Sep. 15, 2003.
Bachar-Lustig et al. "Megadose of T Cell-Depleted Bone Marrow Overcomes MHC Barriers in Sublethally Irradiated Mice", Nature Medicine, 1(12): 1268-1273, Dec. 1995.
Berger et al. "Adoptive Transfer of Effector CD8+ T Cells Derived from Central Memory Cells Establishes Persistent T cell Memory in Primates", The Journal of Clinical Investigation, 118(1): 294-305, Jan. 2008.
Biocompare "Human CD8+ T Cell Isolation Kit II From Miltenyi Biotec", Biocompare, pp. 1-5, Oct. 30, 2006.
Dutton et al. "T Cell Memory", Annual Review of Immunology, 16: 201-223, 1998. p. 203, 2nd Para.
Fujiwara "Adoptive Immunotherapy for Hematological Malignancies Using T Cells Gene-Modified to Express Tumor Antigen-Specific Receptors", Pharmaceuticals, 7(12): 1049-1068, Dec. 15, 2014.
Gilham et al. "Adoptive T-Cell Therapy for Cancer in the United Kingdom: A Review of Activity for the British Society of Gene and Cell Therapy Annual Meeting 2015", Human Gene Therapy, 26(5): 276-285, Published Online Apr. 10, 2015.

Gouble et al. "In Vivo Proof of Concept of Activity and Safety of UCART19, an Allogeneic 'Off-the-Shelf' Adoptive T-Cell Immunotherapy Against CD 19+ B-Cell Leukemias", Blood, 124(21): 4689, Dec. 6, 2014.
Grigg et al. "Graft-Versus-Lymphoma Effects: Clinical Review, Policy Proposal, and Immunobiology", Biology of Blood and Marrow Transplantation, 10: 579-590, 2004.
Gur et al. "Immune Regulatory Activity of CD34+ Progenitor Cells: Evidence for A Deletion-Based Mechanism Mediated by TNF-{Alpha}", Blood, 105(6): 2585-2593, Mar. 15, 2005.
Gur et al. "Tolerance Induction by Megadose Hematopoietic Progenitor Cells: Expansion of Veto Cells by Short-Term Culture of Purified Human CD34+ Cells", Blood, 99(11): 4174-4181, Jun. 1, 2002.
Handgretinger et al. "Megadose Transplantation of Purified Peripheral Blood CD34+ Progenitor Cells From HLA-Mismatched Parental Donors in Children", Bone Marrow Transplantation, 27: 777-783, 2001.
Harwerth et al. "Monoclonal Antibodies Directed to the ErbB-2 Receptor Inhibit In Vivo Tumour Cell Growth", British Journal of Cancer, 68(6): 1140-1145, Dec. 1993.
Hecht et al. "Embryonic Pig Pancreatic Tissue for the Treatment of Diabetes in A Nonhuman Primate Model", Proc. Natl. Acad. Sci. USA, PNAS, XP009122169, 106(21): 8659-8664, May 26, 2009. p. 8663, col. l, Para 2.
Ho et al. "Adoptive Therapy With CD8+ T Cells: It May Get by With A Little Help From Its Friends", the Journal of Clinical Investigation, 110(10): 1415-1417, Nov. 2002.
Huarte et al. "Ex Vivo Expansion of Tumor Specific Lymphocytes With IL-15 and IL-21 for Adoptive Immunotherapy in Melanoma", Cancer Letters, 285: 80-88, 2009. Abstract, p. 80, Left Right Col. 2nd Para, Section 2.4.
Kawai et al. "HLA-Mismatched Renal Transplantation Without Maintenance Immunosuppression", The New England Journal of Medicine, XP002562461, 358(4): 353-361, Jan. 24, 2008. Abstract, p. 353-354, col. 1, Para 2, Table 1.
Lapidot et al. "Enhancement by Dimethyl Myleran of Donor Type Chimerism in Murine Recipients of Bone Marrow Allografts", Blood, 73(7): 2025-2032, May 15, 1989.
Lapidot et al. "Enhancement by Dimethyl Myleran of Donor type Chimerism in Murine Resipients of Bone Marrow Allografts", Blood, 73(7): 2025-2032, May 15, 1989.
Lask et al. "TCR Independent Killing of B Cell Malignancies by Anti-3rd Party CTLs: Rapid Conjugate Formation Via ICAM1-LFA1 Leads to Slow Induction of Apoptosis Upon MHC-CD8 Engagement", Journal of Immunology, XP009156306, 187(4): 2006-2014, Aug. 15, 2011.
Li et al. "IL-21 Influences the Frequency, Phenotype, and Affinity of the Antigen-Specific CD8 T Cell Response", The Journal of Immunology, 175: 2261-2269, 2005. Abstract, Materials and Methods: Induction of Human Ag-Specific CD8+ T Cells.
Markley et al. "IL-7 and IL-21 Are Superior to IL-2 and IL-15 in Promoting Human T Cell-Mediated Rejection of Systematic Lymphoma in Immunodeficient Mice", Blood, XP009165652, 115(17): 3508-3519, Apr. 29, 2010. p. 3509, col. 2, Par 2.
Ophir et al. "Induction of Tolerance in Organ Recipients by Hematopoietic Stem Cell Transplantation", International Immunopharmacology, XP026088865, 9(6): 694-700, Jun. 1, 2009. Figs.3, 6.
Ophir et al. "Induction of Tolerance to Bone Marrow Allografts by Donor-Derived Host Nonreactive Ex Vivo Induced Central Memory CD8 T Cells", Blood, XP009165643, 115(10): 2095-2104, Mar. 11, 2010. Abstract, p. 2096, col. 1, Para 2.
Ophir et al. "Induction of Transplantation Tolerance in Haploidenical Transplantation Under Reduced Intensity Conditioning: The Role of Ex-Vivo Generated Donor CD8+ T Cells With Central Memory Phenotype", Best Practice & Research Clinical Haematology, XP002829486, 24(3): 393-401, Jul. 13, 2011. p. 396, Fig.3.
Pilat et al. "Treg-Therapy Allows Mixed Chimerism and Transplantation Tolerance Without Cytoreductive Conditioning", American Journal of Transplantation, 10: 751-762, 2010.
Rachamim et al. "Tolerance Induction by 'Megadose' Hematopoietic Transplants. Donor-Type CD34 Stem Cells Induce Potent Specific

(56) References Cited

OTHER PUBLICATIONS

Reduction of Host antiDonor Cytotoxic T Lymphocyte Precursors in Mixed Lymphocyte Culture", Transplantation, 65(10): 1386-1393, May 27, 1998.
Reich-Zeliger et al. "Anti-Third Party CD8+ CTLs as Potent Veto Cells: Coexpression of CD8 and FasL Is A Prerequisite", Immunity, 13: 507-515, Oct. 2000.
Reich-Zeliger et al. "Tolerance Induction by Veto CTLs in the TCR Transgenic 2C Mouse Model. I. Relative Reactivity of Different Veto Cells", The Journal of Immunology, 173(11): 6654-6659, Dec. 2004.
Reisner et al. "Bone Marrow Transplantation Across HLA Barriers by Increasing the Number of Transplanted Cells", Immunology Today, 16(9): 437-440, 1995.
Reisner et al. "Demonstration of Clonable Alloreactive Host T Cells in A Primate Model for Bone Marrow Transplantation", Proc. Natl. Acad. Sci. USA, 83: 4012-415, Jun. 1986.
Reisner et al. "Stem Cell Escalation Enables HLA-Disparate Haematopoietic Transplants in Leukaemia Patients", Immunology Today, 20(8): 343-347, Aug. 1999.
Roncarolo et al. "Regulatory T-Cell Immunotherapy for Tolerance To Self Antigens and Alloantigens in Humans", Nature Reviews Immunology, 7(8): 585-598, Aug. 2007.
Santegoets et al. "In Vitro Priming of Tumor-Specific Cytotoxic T Lymphocytes Using Allogeneic Dendritic Cells Derived From the Human MUTZ-3 Cell Line", Cancer Immunol Immunother, 55(12): 1480-1490, Published Online Feb. 9, 2006.
Scandling et al. "Tolerance and Chimerism After Renal and Hematopoietic-Cell Tranplantation", The New England Journal of Medicine, XP002562462, 358(4): 362-368, Jan. 24, 2008. Abstract, p. 363-365, Fig.3, Abstract, p. 362, Para 1, 3-p. 363, Left col. Para 2, Right col. Para 2, 4, p. 365, Left col. Para 2, p. 367, Discussion, Figs.2, 3.
Sharpe et al. "Genetically Modified T Cells in Cancer Therapy: Opportunities and Challenges", Disease Models and Mechanisms, 8(4): 337-350, Apr. 2015.
Tchorsh-Yutsis et al. "Pig Embryonic Pancreatic Tissue as A Source for Transplantation in Diabetes. Transient Treatment With Anit-LFA1, Anit-CD48, and FTY720 Enables Long-Term Graft Maintenance in Mice With Only Mild Ongoing Immunosuppression", Diabetes, XP009122170, 58(7): 1585-1594, Jul. 1, 2009. Figs.5, 7, Table 1.
Uharek et al. "Influence of Cell Dose and Graft-Versus-Host Reactivity on Rejection Rates After Allogeneic Bone Marrow Transplantation", Blood, 79(6): 1612-1621, Mar. 15, 1992.
Weninger et al. "Migratory Properties of Naive, Effector, and Memory CD8+ T Cells", Journal of Experimental Medicine, 12(6): 953-966, Oct. 1, 2001.
Wherry et al. "Lineage Relationship and Protective Immunity of Memory CD8 T Cell Subsets", Nature Immunology, XP002562463, 4(3): 225-234, Mar. 2003. p. 232-233, Figs. 1-4.
Woelfl et al. "Primed Tumor-Reactive Multifunctional CD62L+ Human CD8+ T Cells for Immunotherapy", Cancer Immunology, Immunotherapy, 60(2): 173-186, Feb. 2011.
Xie "The Development of the PBSC Transplantation", Railway Medical Journal, 29(5): 281-283, Jan. 31, 2001. & English Translation.
Yang et al. "In Vitro Generated Anti-Tumor T Lymphocytes Exhibit Distinct Subsets Mimicking In Vivo Antigen-Experienced Cells", Cancer Immunology, Immunotherapy: CII, XP009165653, 60(5): 739-749, May 2011.
Zeng et al. "Synergy of IL-21 and IL-15 in Regulating CD8+ T Cell Expansion and Function", The Journal of Experimental Medicine, 201(1): 139-148, Jan. 3, 2005.
Official Action dated Jan. 2, 2020 From the U.S. Appl. No. 15/825,275. (55 pages).
International Preliminary Report on Patentability dated Aug. 1, 2019 From the International Bureau of WIPO Re. Application No. PCT/IL2018/050071. (10 Pages).

Official Action dated Sep. 19, 2019 From the U.S. Appl. No. 15/744,881. (46 Pages).
Lask et al. "A New Approach For Eradication of Residual Lymphoma Cells By Host Nonreactive Anti-Third-Party Central Memory CDS T Cells", Blood, 121(15): 3033-3040, Published Online Feb. 27, 2013.
Ophir et al. "Induction of Transplantation Tolerance in Haploidenical Transplantation Under Reduced Intensity Conditioning: The Role of Ex-Vivo Generated Donor Cos+ T Cells with Central Memory Phenotype", Best Practice & Research Clinical Haematology 24(3): 393-401, Jul. 13, 2011.
Ophir et al. "Murine Anti-Third-Party Central-Memory CDS+ T Cells Promote Hematopoietic Chimerism Under Mild Conditioning: Lymph-Node Sequestration and Deletion of Anti-Donor T Cells", Blood. 121(7): 1220-1228, Prepublished online Dec. 5, 2012.
Or-Geva et al. "Towards Off-The-Shelf Genetically Modified T Cells: Prolonging Functional Engraftment in Mice by CD8 Veto T Cells", Leukemia, 32(4):1039-1041, Published Online Nov. 20, 2017.
Communication Pursuant to Article 94(3) EPC dated Apr. 24, 2020 From the European Patent Office Re. Application No. 16750269.9. (4 Pages).
Communication Pursuant to Article 94(3) EPC dated Mar. 27, 2020 From the European Patent Office Re. Application No. 16745186.3. (7 Pages).
Final Official Action dated May 4, 2020 from the U.S. Appl. No. 15/744,881. (10 pages).
Notice of Allowance dated May 14, 2020 from the U.S. Appl. No. 15/873,943. (74 pages).
Official Action dated Apr. 21, 2020 from the U.S. Appl. No. 15/242,666. (20 pages).
Bachar-Lustig et al. "Next Generation Veto Cells for Non-Myeloablative Haploidentical HSCT: Combining Anti-Viral and Graft Facilitating Activity", Experimental Transplantation: Basic Biologigy, Pre-Clinical Models: Poster 2, Dec. 2, 2016.
Notice of Reasons for Refusal dated Jun. 9, 2020 From the Japan Patent Office Re. Application No. 2018-501339 and Its Translation Into English. (18 Pages).
Notification of Office Action dated Jun. 12, 2020 From the National Intellectual Property Administration of the People's Republic of China Re. Application No. 201610307275.9 and Its Translation Into English. (21 Pages).
Final Official Action dated Aug. 31, 2020 from the U.S. Appl. No. 15/825,275. (24 pages).
Miltenyi Biotec "CDS+ T Cell Isolation Kit", Retrieved from the Internet, 2 pages.
Stanciu et al. "Isolation of T-Cell Subsets by Magnetic Cell Sorting (MACS)", Methods in Molecular Biology (134): 133-141, 2000.
Search Report and Written Opinion dated Oct. 30, 2020 From the Service Publico Federal, Ministerio da Economia, Institute Nacional da Propriedade Industrial do Brasil Re. Application No. BR112014005355-3 and Its Translation of Written Opinion Into English. (6 Pages).
Notification of Office Action dated Apr. 12, 2021 From the National Intellectual Property Administration of the People's Republic of China Re. Application No. 201680053579.5 and Its Translation Into English. (19 Pages).
Search Report and Opinion dated Sep. 14, 2020 From the Service Publico Federal, Ministerio da Economia, Institute Nacion da Propriedade Industrial do Brasil Re. Application No. BR112013005756-4 and Its Translaton of Opinion Into English. (6 Pages).
Hearing Notice Dated Mar. 11, 2021 From the Government of India, Intellectual Property India, Patent Office, Intellectual Property Building Re. Application No. 577/MUMNP/2014. (2 Pages).
Final Official Action dated Feb. 2, 2021 From the U.S. Appl. No. 15/242,666. (41 Pages).
Rosenberg "Adoptive Cell Transfer: A Clinical Path to Effective Cancer Immunotherapy", Nature Reviews Cancer, 8(4):299-308, Published: Apr. 2008.
Office Action dated Oct. 21, 2020 From the Israel Patent Office Re. Application No. 256916 and Its Translation Into English.

(56) References Cited

OTHER PUBLICATIONS

Advisory Action dated Sep. 17, 2020 from the U.S. Appl. No. 15/744,881. (8 pages).
Notification of Office Action and Search Report dated Aug. 21, 2020 From the State Intellectual Property Office of the People's Republic of China Re. Application No. 201680053579.5. (12 Pages).
Translation Dated Sep. 24, 2020 of Notification of Office Action and Search Report dated Aug. 21, 2020 From the State Intellectual Property Office of the People's Republic of China Re. Application No. 201680053579.5. (11 Pages).
Masopust et al. "The Role of Programming in Memory T-Cell Development", Current Opinion in Immunology, 16(2); 217-225, Apr. 2004.
Notification of Office Action dated Mar. 3, 2021 From the National Intellectual Property Administration of the People's Republic of China Re. Application No. 201610307275.9 and Its Translation Into English. (14 Pages).
Notification of Office Action and Search Report dated Oct. 28, 2020 From the National Intellectual Property Office of the People's Republic of China Re. Application No. 201680053580.8 and Its Translation Into English. (41 Pages).
Zhao "Innovation and Prospects of Chimeric Antigen Receptor (CAR) Technique in Hematological Malignancies Immunotherapy", Chinese Master's Thesis Full-Text Database, Medical and Hygiene Technology, 11: E072-E090, May 30, 2014. & English Abstract.
Notification of Office Action and Search Report dated Feb. 26, 2019 From the National Intellectual Property Administration of the People's Republic of China Re. Application No. 201610307275.9 and Its Translation Into English. (20 Pages).

\* cited by examiner

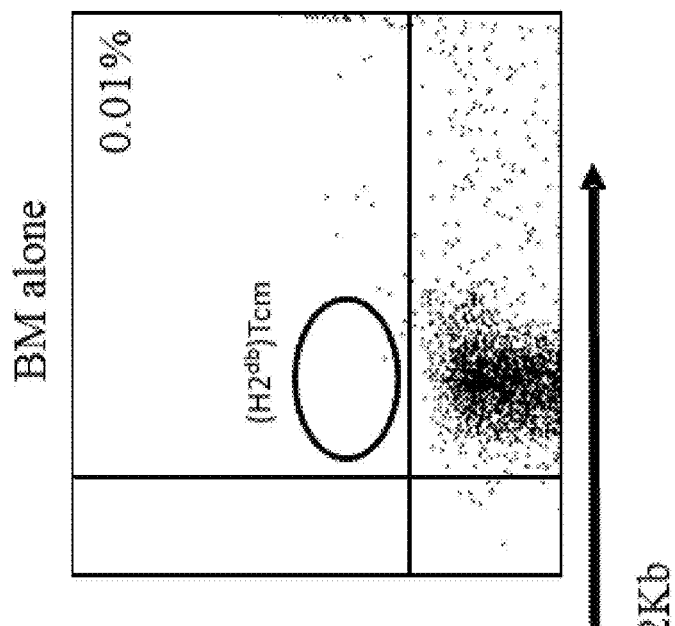
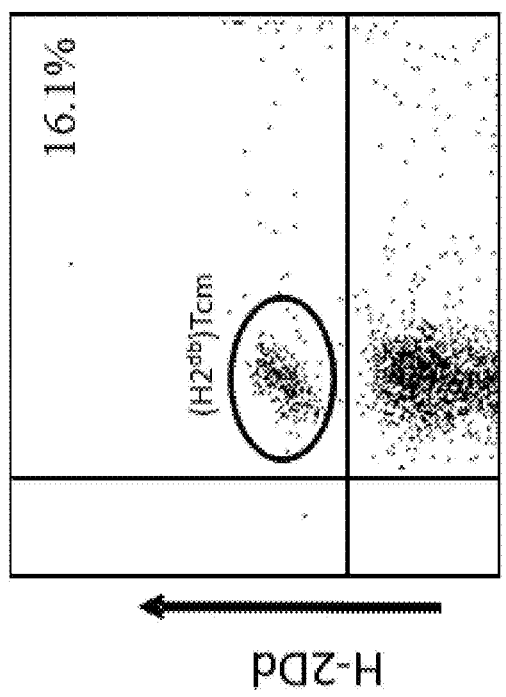

GENETICALLY MODIFIED ANTI-THIRD PARTY CENTRAL MEMORY T CELLS AND USE OF SAME IN IMMUNOTHERAPY

RELATED APPLICATIONS

This application is a National Phase of PCT Patent Application No. PCT/IL2016/050775 having International filing date of Jul. 14, 2016, which claims the benefit of priority under 35 USC § 119(e) of U.S. Provisional Patent Application Nos. 62/193,229 and 62/193,207 both filed on Jul. 16, 2015. The contents of the above applications are all incorporated by reference as if fully set forth herein in their entirety.

FIELD AND BACKGROUND OF THE INVENTION

The present invention, in some embodiments thereof, relates to genetically modified tolerance inducing central memory T-lymphocytes transduced to express a cell surface receptor and, more particularly, but not exclusively, to the use of same in immunotherapy.

Adoptive cell therapy (ACT) is a therapeutic procedure in which lymphocytes (e.g. T cells) are administered to patients in order to treat cancer or viral infections.

This approach requires the ex vivo generation of tumor- or viral-specific T cells and infusion of same to patients. In order to support the acceptance of the T cells, the patient is typically also treated with conditioning protocols, for example, preconditioning protocols (e.g. irradiation or chemotherapy) and/or administration of lymphocyte growth factors (such as IL-2). Many methods have been described for generating tumor specific lymphocytes with the two main approaches being expansion of antigen specific T cells or redirection of T cells using genetic engineering.

According to one approach, tumor infiltrating lymphocytes (TIL) are isolated from a patient's own tumor mass (e.g. melanoma or renal cancer), are expanded ex vivo and are re-infused back into the patient. TILs are a promising source of cells as they are a mixed set of the patient's own cells that have T-cell receptors (TCRs) specific for the tumor associated antigens (TAAs) present on the tumor. However, they are only applicable in cases where T cells can be isolated from a tumor mass.

This approach has been promising in treating metastatic melanoma.

According to another approach, gene modification is used to redirect lymphocytes against tumors via the use of transgenic TCR chains or chimeric receptors. Currently, retroviral or lentiviral, or electroporational transfer of chimeric antigen receptors (CARs) whose target recognition is dependent on a single-chain variable region domain of a monoclonal antibody (scFv) or that of a T-cell receptor (TCR) is typically used for stable production of therapeutic T cells (CAR-T cells or TCR-T cells, respectively) [Fujiwara, Pharmaceuticals (2014) 7: 1049-1068].

The TCR transgenic cells (TCR-T) require a specific HLA molecule for recognition of the target antigen (i.e., HLA restriction) and have the ability to recognize intracellular proteins, providing a broad array of target tumor-associated antigens or viral antigens. The therapeutic quality of the TCR-T cells is dependent on their avidity. To create higher avidity several strategies have been implemented, including, the use of selected TCRs from immunized human HLA transgenic mice with relevant epitopes and/or insertion of targeted mutations in CDR regions 2 or 3 in the variable regions of the TCR α/β chains that interact with the HLA/epitope complex [Fujiwara, Pharmaceuticals (2014) supra].

Alternatively, CAR-T cells are not HLA restricted. The construct of the chimeric receptor (chimeric antigen receptor—CAR) is typically composed of an extracellular antigen-binding domain, a transmembrane domain and a cytoplasmic signaling domain. The original chimeric receptor (i.e. 'first-generation') was composed of a scFv fragment fused to an intracellular domain from the CD3 ζ-chain.

A 'second generation' chimeric receptor was also generated which adds an intracellular signaling domain, from various co-stimulatory protein receptors (e.g. CD28, CD137, 4-1BB, ICOS), to the cytoplasmic tail of the CAR to provide additional signals to the T cell. Preclinical studies have indicated that the 'second generation' CARs improved the anti-tumor activity of T cells. A "third-generation" CARs was recently generated which combine multiple signaling domains, such as CD3zeta-CD28-4-1BB or CD3zeta-CD28-OX40, to further augment potency.

Tumor specific CARs targeting a variety of tumor antigens are being tested in the clinic for treatment of a variety of different cancers. Examples of these cancers and their antigens that are being targeted includes follicular lymphoma (CD20 or GD2), neuroblastoma (CD171), non-Hodgkin lymphoma (CD20), lymphoma (CD19), glioblastoma (IL13Rα2), chronic lymphocytic leukemia or CLL and acute lymphocytic leukemia or ALL (both CD19). CARs demonstrating activity against solid tumors including ovarian, prostate, breast, renal, colon, neuroblastoma and others are under investigation. Virus specific CARs have also been developed to attack cells harboring virus such as HIV. For example, a clinical trial was initiated using a CAR specific for Gp100 for treatment of HIV (Chicaybam, Ibid).

A major objective is to apply ACT, including genetically modified T cells, using fully or partially mismatched allogeneic cells without resorting to bone marrow transplantation.

Various approaches have been contemplated for modifying T-cells for adoptive cell therapy, some are described in Gilham et al., Human Gene Therapy (2015) 26:276-285; in Sharpe and Mount, Disease Models and Mechanisms (2015) 8:337-350 and in Gouble et al. Blood (2014) 124(21) 4689.

Various approaches have been contemplated for generation of tolerance inducing cells devoid of graft versus host (GVH) activity and the use of same for graft transplantation, some are summarized infra.

One approach developed to generate veto CTLs devoid of GVH activity was described by Reisner and co-workers, in which CTLs were stimulated against $3^{rd}$-party stimulators in the absence of exogenous IL-2. This approach was based on the observation that only activated cytotoxic T lymphocyte precursors (CTLp) were capable of surviving the IL-2 deprivation in the primary culture (IL-2 starvation results in apoptosis of non-induced T cells). This method was shown in vitro and in vivo to deplete GVH reactivity from the anti-$3^{rd}$ party veto CTLs [PCT Publication No. WO 2001/049243, Bachar-Lustig et al., Blood. 2003; 102:1943-1950; Aviner et al., Hum Immunol. (2005) 66:644-652]. Introduction of these anti-$3^{rd}$ party veto CTLs into a recipient (along with a transplant) prevented graft rejection without inducing graft versus host disease (GVHD) (PCT Publication No. WO 2001/049243).

PCT Publication No. WO 2010/049935 discloses an isolated population of cells comprising non-GVHD inducing anti-third party cells having a central memory T-lymphocyte (Tcm) phenotype, the cells being tolerance-inducing cells and capable of homing to the lymph nodes following transplantation.

PCT Publication No. WO 2013/035099 discloses new methods of generating an isolated population of cells comprising anti-third party cells having central memory T-lymphocyte (Tcm) phenotype, the cells being tolerance-inducing cells and/or endowed with anti-disease activity, and capable of homing to the lymph nodes following transplantation.

SUMMARY OF THE INVENTION

According to an aspect of some embodiments of the present invention there is provided an isolated cell having a central memory T-lymphocyte (Tcm) phenotype, the cell being tolerance-inducing cell and capable of homing to the lymph nodes following transplantation, the cell being transduced to express a cell surface receptor comprising a T cell receptor signaling module.

According to an aspect of some embodiments of the present invention there is provided an isolated cell having a central memory T-lymphocyte (Tcm) phenotype, the cell being tolerance-inducing cell and capable of homing to the lymph nodes following transplantation, the cell being transduced to express a chimeric antigen receptor (CAR).

According to an aspect of some embodiments of the present invention there is provided an isolated cell having a central memory T-lymphocyte (Tcm) phenotype, the cell being tolerance-inducing cell and capable of homing to the lymph nodes following transplantation, the cell being transduced to express a chimeric antigen receptor (CAR), wherein the CAR comprises a co-stimulatory domain.

According to an aspect of some embodiments of the present invention there is provided an isolated cell having a central memory T-lymphocyte (Tcm) phenotype, the cell being tolerance-inducing cell and capable of homing to the lymph nodes following transplantation, the cell being transduced to express a chimeric antigen receptor (CAR), wherein the CAR comprises at least two co-stimulatory domains.

According to an aspect of some embodiments of the present invention there is provided a method of generating the isolated cell of some embodiments of the invention, the method comprising transducing a cell having a central memory T-lymphocyte (Tcm) phenotype, the cell being tolerance-inducing cell and capable of homing to the lymph nodes following transplantation, with a polynucleotide encoding the cell surface receptor comprising a T cell receptor signaling module or the chimeric antigen receptor (CAR).

According to an aspect of some embodiments of the present invention there is provided a population of cells comprising the isolated cell of some embodiments of the invention.

According to an aspect of some embodiments of the present invention there is provided a pharmaceutical composition comprising the population of cells of some embodiments of the invention and a pharmaceutically active carrier.

According to an aspect of some embodiments of the present invention there is provided a method of treating a disease in a subject in need thereof, the method comprising administering to the subject a therapeutically effective amount of the population of cells of some embodiments of the invention, thereby treating the subject.

According to an aspect of some embodiments of the present invention there is provided a therapeutically effective amount of the population of cells of some embodiments of the invention for use in treating a disease in a subject in need thereof.

According to some embodiments of the invention, the method is effected ex-vivo.

According to some embodiments of the invention, the cell is transduced with a vector comprising the polynucleotide.

According to some embodiments of the invention, the polynucleotide encodes for a transgenic T cell receptor (tg-TCR) or a chimeric antigen receptor (CAR).

According to some embodiments of the invention, the cell having the central memory T-lymphocyte (Tcm) phenotype is an anti-third party cell.

According to some embodiments of the invention, the cell surface receptor comprises a transgenic T cell receptor (tg-TCR) or a chimeric antigen receptor (CAR).

According to some embodiments of the invention, the CAR comprises an antigen binding domain being an antibody or an antigen-binding fragment.

According to some embodiments of the invention, the antigen-binding fragment is a Fab or a scFv.

According to some embodiments of the invention, the CAR comprises a CD3ζ.

According to some embodiments of the invention, the CAR comprises at least one co-stimulatory domain selected from the group consisting of CD28, CD134/OX40, CD137/4-1BB, Lck, ICOS and DAP10.

According to some embodiments of the invention, the CAR comprises at least two co-stimulatory domains selected from the group consisting of CD28, CD134/OX40, CD137/4-1BB, Lck, ICOS and DAP10.

According to some embodiments of the invention, the cell surface receptor or the CAR binds an antigen selected from the group consisting of a tumor antigen, a viral antigen, a bacterial antigen, a fungal antigen, a protozoa antigen, a parasite antigen, an allergic antigen and an autoimmune antigen.

According to some embodiments of the invention, the tumor antigen is associated with a solid tumor.

According to some embodiments of the invention, the tumor antigen is associated with a hematologic malignancy.

According to some embodiments of the invention, the tumor antigen is selected from the group consisting of CD19, CD20, CD22, ROR1, mesothelin, CD33/IL3Rα, c-Met, PSMA, Glycolipid F77, EGFRvIII, Her2, GD2, gp100, p53, carcinoembryonic antigen (CEA), MART-1, Telomerase reverse transcriptase (TERT), Claudin-6, Receptor tyrosine-protein kinase extracellular domain (ErbB2-ECD), Receptor tyrosine-protein kinase intracellular domain (ErbB2-ICD), Histone H1.2, Histone H4, Tyrosinase, alphafetoprotein (AFP), MAGE A3, AIM-2a, AFP, ART-4, CLCA2, Cyp-B, EphA2, hTERT, iCE, FGF-5, G250, GnT-V, HST-2 (FGF-6), Livin (ML-IAP), MUC1, MUC2, PRAME, PSMA, P15, RAGE, RU1, RU2, SART-1, SART-3, SART-2, SOX10, Survivin, Survivin-2Bg, TRG, Neo-PAP, CAMEL and NY-ESO-1.

According to some embodiments of the invention, the viral antigen is of a virus selected from the group consisting of human immunodeficiency virus (HIV), influenza, Cytomegalovirus (CMV), T-cell leukemia virus type 1 (TAX), hepatitis C virus (HCV), influenza virus, rabies virus, herpes virus, papilloma virus, hepatitis viruses, varicella virus, encephalitis virus, cytomegalo virus, ebola virus, human T-lymphotropic virus (HTLV), rubella virus, measles virus, rabies virus, lymphocytic choriomeningitis (LCM), rotavirus, mumps virus, adenovirus, Adenovirus-3 (HADV-3), Adenovirus-5 (HADV-5), Adeno associated virus 6 (AAV6), Adeno associated virus 8 (AAV8), BK polyomavirus (BKV), *Candida*, Epstein-Barr virus (EBV), Human Herpesvirus (HHV), Vericella-zoster virus (VZV) and hepatitis B virus (HBV).

According to some embodiments of the invention, the autoimmune antigen is associated with a disease selected from the group consisting of type 1 diabetes, multiple sclerosis, lupus, rheumatoid arthritis, Crohn's disease, celiac and stroke.

According to some embodiments of the invention, the cell is further genetically modified to repress expression of at least one endogenous immunological checkpoint gene in the cell.

According to some embodiments of the invention, the immunological checkpoint gene is selected from the group consisting of a PD or CTLA gene.

According to some embodiments of the invention, the cell having a central memory T-lymphocyte (Tcm) phenotype, the cell being tolerance-inducing cell and capable of homing to the lymph nodes following transplantation, is generated by a method comprising: (a) contacting peripheral blood mononuclear cells (PBMC) with a third party antigen or antigens in the presence of IL-21 so as to allow enrichment of antigen reactive cells; and (b) culturing the cells resulting from step (a) in the presence of IL-21, IL-15 and IL-7 so as to allow proliferation of anti-third party cells comprising the central memory T-lymphocyte (Tcm) phenotype, thereby generating the cell having a Tcm phenotype, the cell being tolerance-inducing cell and capable of homing to the lymph nodes following transplantation.

According to some embodiments of the invention, the method further comprises: (c) separating the cells resulting from step (b) into single cell suspensions.

According to some embodiments of the invention, the method further comprises selecting for activated cells following step (a) and prior to step (b).

According to some embodiments of the invention, the selecting for activated cells is effected by selection of CD137+ and/or CD25+ cells.

According to some embodiments of the invention, the Tcm phenotype comprises a $CD3^+$, $CD8^+$, $CD62L^+$, $CD45RA^-$, $CD45RO^+$ signature.

According to some embodiments of the invention, at least 50% of the isolated cells are CD3+CD8+ cells of which at least 50% have the signature.

According to some embodiments of the invention, the disease is selected from the group consisting of a malignant disease, a viral disease, a bacterial disease, a fungal disease, a protozoa disease, a parasite disease, an allergic disease and an autoimmune disease.

According to some embodiments of the invention, the malignant disease is a solid tumor or tumor metastasis.

According to some embodiments of the invention, the malignant disease is a hematological malignancy.

According to some embodiments of the invention, the hematological malignancy comprises a leukemia or a lymphoma.

According to some embodiments of the invention, the malignant disease is selected from the group consisting of a leukemia, a lymphoma, a myeloma, a melanoma, a sarcoma, a neuroblastoma, a colon cancer, a colorectal cancer, a breast cancer, an ovarian cancer, an esophageal cancer, a synovial cell cancer and a pancreatic cancer.

According to some embodiments of the invention, the viral disease is selected from the group consisting of an immunodeficiency virus (HIV), an influenza, a Cytomegalovirus (CMV), a T-cell leukemia virus type 1 (TAX), a hepatitis C virus (HCV) and a hepatitis B virus (HBV).

According to some embodiments of the invention, the autoimmune disease is selected from the group consisting of a type 1 diabetes, a multiple sclerosis, a rheumatoid arthritis, a lupus, a celiac and a stroke.

According to some embodiments of the invention, the population of cells is non-syngeneic with the subject.

According to some embodiments of the invention, the method further comprises conditioning the subject under sublethal, lethal or supralethal conditioning protocol prior to the administering.

According to some embodiments of the invention, the therapeutically effective amount for use further comprises a sublethal, lethal or supralethal conditioning protocol.

According to some embodiments of the invention, the sublethal, lethal or supralethal conditioning is selected from the group consisting of a total body irradiation (TBI), a partial body irradiation, a myeloablative conditioning, a non-myeloablative conditioning, a co-stimulatory blockade, a chemotherapeutic agent and an antibody immunotherapy.

According to some embodiments of the invention, the administering is effected by a route selected from the group consisting of intratracheal, intrabronchial, intraalveolar, intravenous, intraperitoneal, intranasal, subcutaneous, intramedullary, intrathecal, intraventricular, intracardiac, intramuscular, intraserosal, intramucosal, transmucosal, transnasal, rectal and intestinal.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
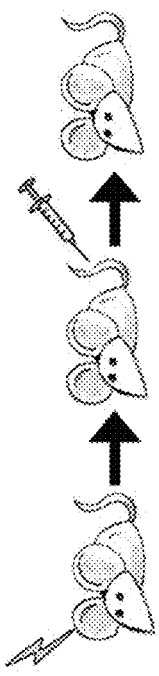
Figure 1B:
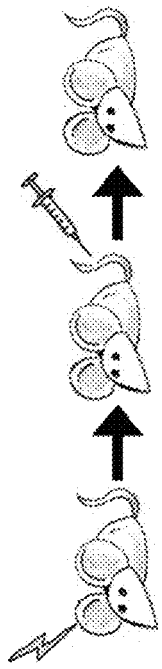
Figure 1C:
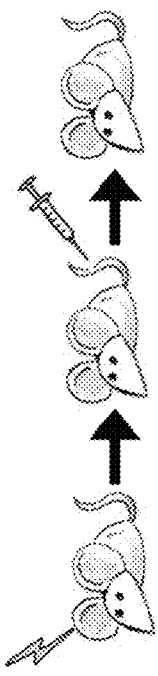

FIGS. 1A-C are schematic illustrations of models for studying the ability of Tcm cells to induce tolerance in the absence of the inductive properties of allogeneic BM. Tcm cell survival and proliferation was analyzed via FACS while downregulation of host CTL activity by Tcm cells was tested using $^{51}Cr$ assay.

FIGS. 2A-B are graphs illustrating the persistence of adoptively transferred F1-Tcm cells under syngeneic bone marrow transplant (BMT) settings. C57BL/6 (H-2b) mice were transplanted as outlined in FIG. 1A. Representative scatter plot of one mouse in each group, showing percentage of Tcm cells in peripheral whole blood of mice, analyzed 60 days post-transplant by FACS using $\alpha H2D^d$ (Donor) and $\alpha H2K^b$ to identify F1($H2D^d$X$H2K^b$)-Tcm cells.

Figure 3:
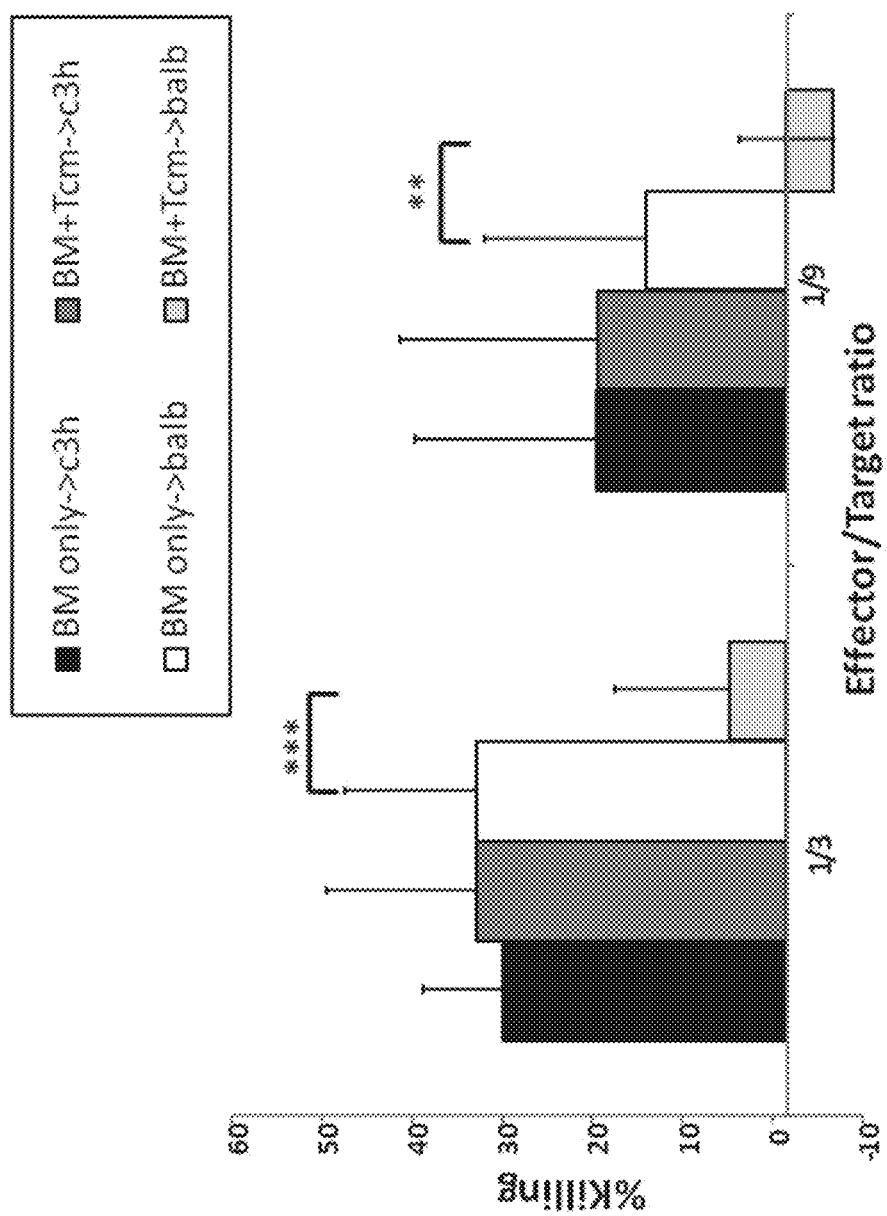

FIG. 3 is a graph illustrating that Tcm cells specifically delete anti-donor T cells from a polyclonal Host T-cell (HTC) population, whilst sparing other HTCs to display cytotoxic activity. Mice were transplanted as outlined in FIG. 1A. Sixty days post transplantation mice were sacrificed, spleens and lymph nodes (LNs) were harvested and cells were selected for CD8+ (and negatively selected for H-2$D^d$ to exclude Tcm). These naive HTC were tested for their killing ability of either C3H (H-2$^k$) or BALB/c (H-2$^d$) targets in a chromium release assay. Bars display killing effect as follows: Killing of C3H target by HTC from mice receiving only BM (black bars, "BM only→C3H") or by cells from mice receiving also Tcm (dark grey bars, "BM+Tcm only→C3H"), or Killing of BALB/c target by HTC from mice receiving only BM (white bars, "BM only→BALB") or by T cells from mice receiving also Tcm (bright grey bars, "BM+Tcm→BALB"). Results are presented as mean±SD of percent killing from 12 wells for each group. Representative experiment out of 2 independent experiments performed is displayed. () Represents p-value of less than 0.01, (*) Represents p-value of less than 0.001.

Figure 4:
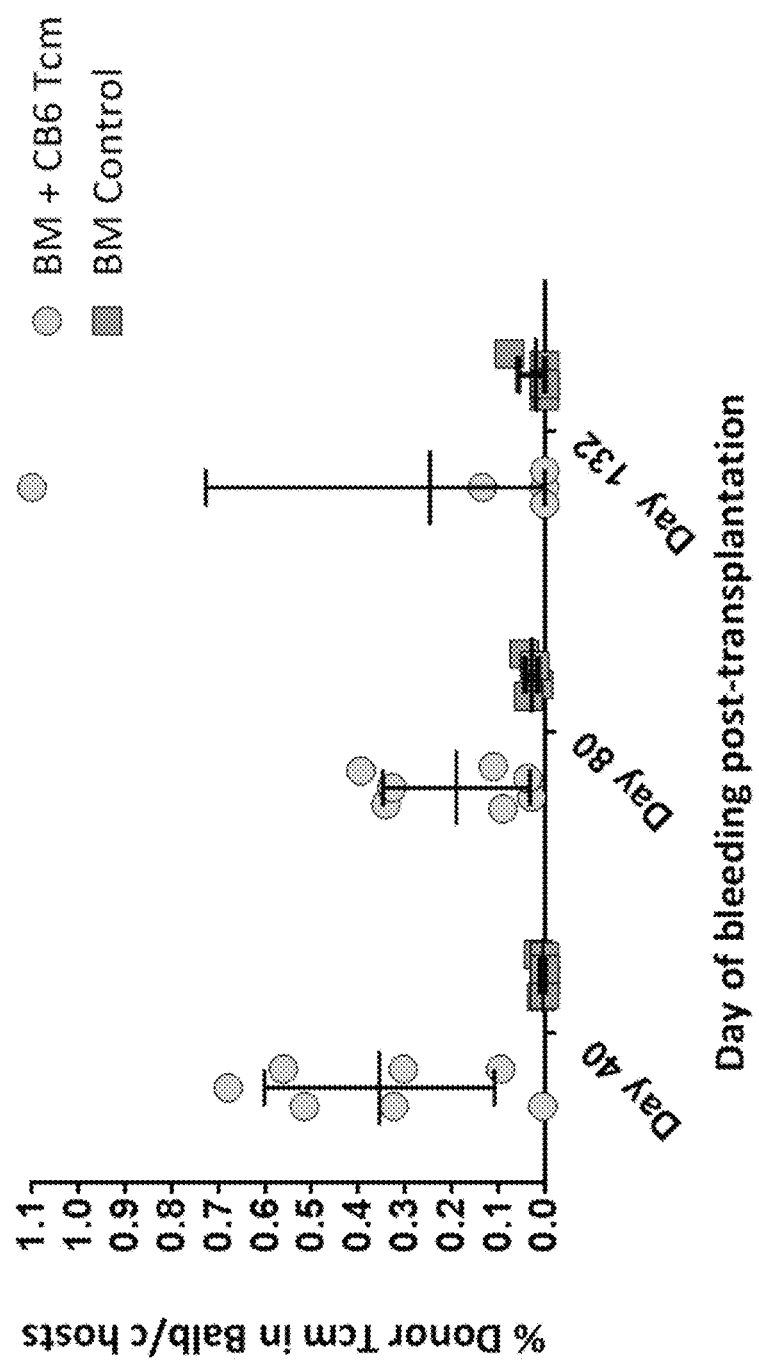

FIG. 4 is a graph illustrating that CB6 F1 derived Tcm cells persist in mice that received sub-lethal 5.5 Gy TBI with syngeneic T cell depleted bone marrow (TDBMT). Balb/c (H2$D^d$) mice were sub-lethally (5.5 Gy) irradiated and transplanted as described in FIG. 1B. Peripheral blood was analyzed 40, 80 and 132 days post-transplant by FACS using $\alpha H2D^d$ (Host) and $\alpha H2K^b$ to identify H2$^{db}$ F1-Tcm cells. Scatter plot showing the percentage of CB6 Tcm cells in each mouse, each dot represents the Tcm cell population in one mouse belonging to the appropriate group, showing the mean and SD of each group.

Figure 5:
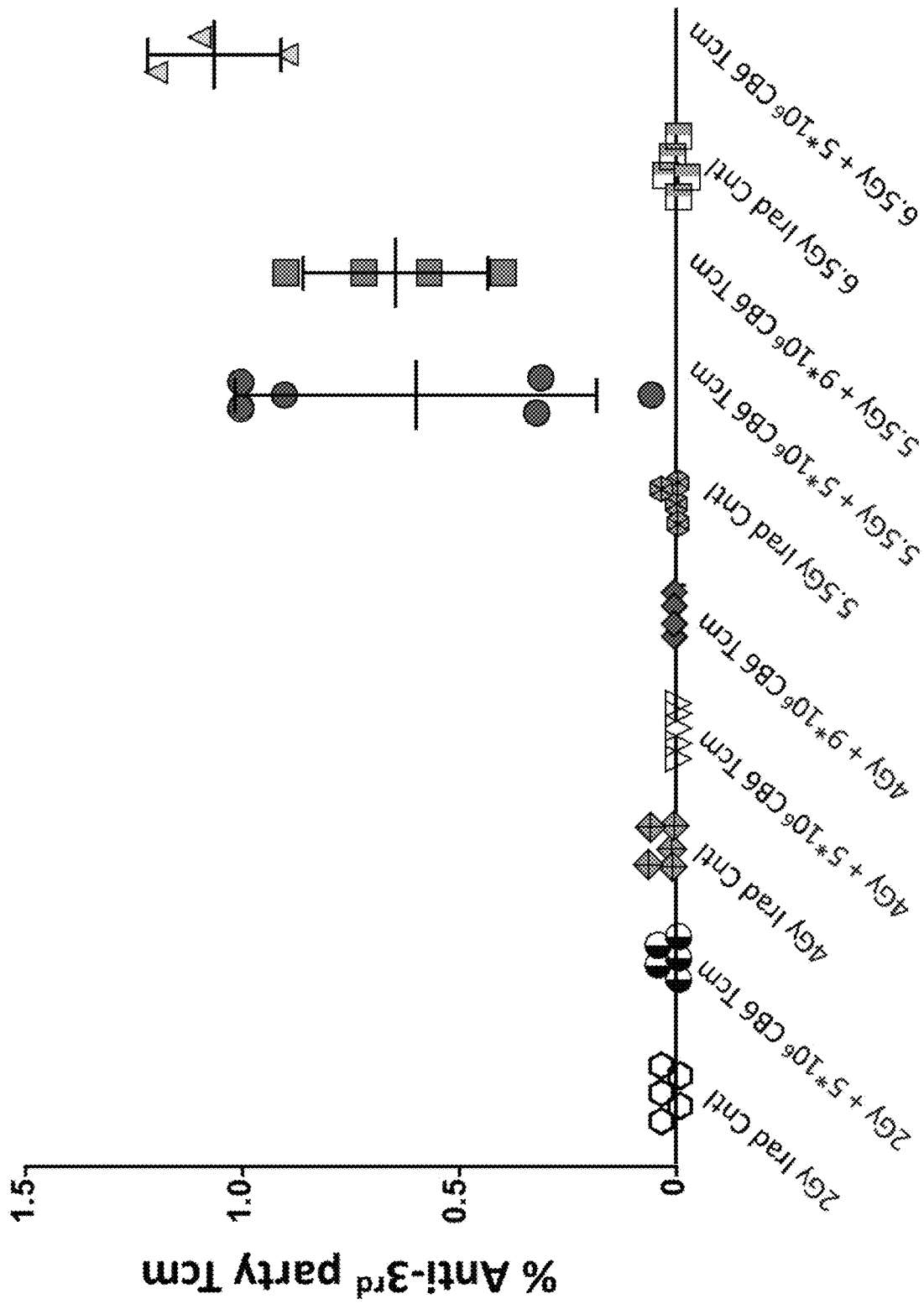

FIG. 5 is a graph illustrating calibration of irradiation dose allowing for Tcm cell survival without TDBMT. Balb/c (H2$D^d$) mice were sub-lethally irradiated with 2/4/5.5/6.5 Gy on day −1. On day 0 mice received 5×10$^6$ or 9×10$^6$ F1 CB6 (H-2$^{db}$) Tcm cells adoptively transferred to the tail vein of the mice. Scatter plot depicting percentage of CB6 Tcm cells in peripheral whole blood of Balb/c host mice, analyzed 42 days post-transplant by FACS using $\alpha H2D^d$ (Host) and $\alpha H2K^b$ to identify H2$^{db}$ F1-Tcm cells. Mean and SD are or each group are shown.

Figure 6B:
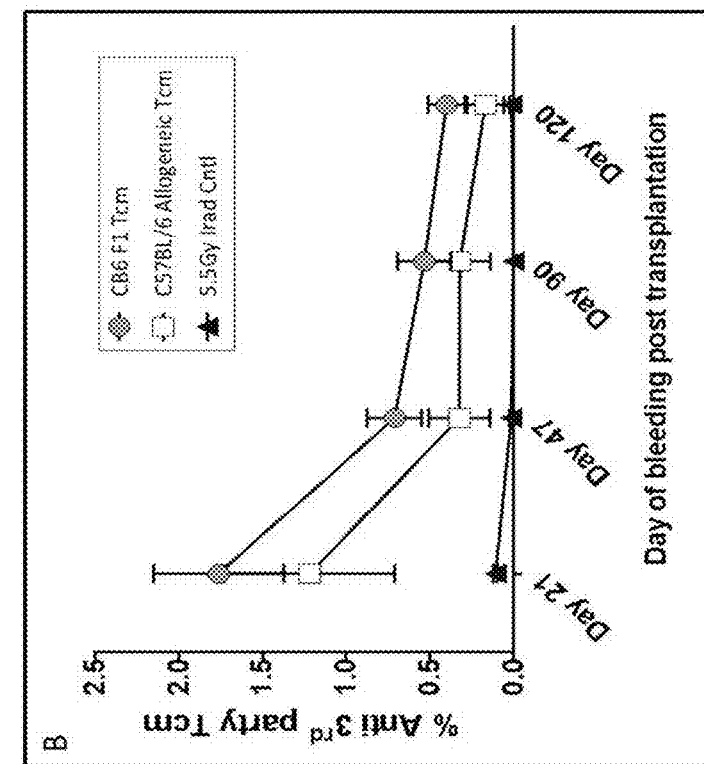
Figure 6A:
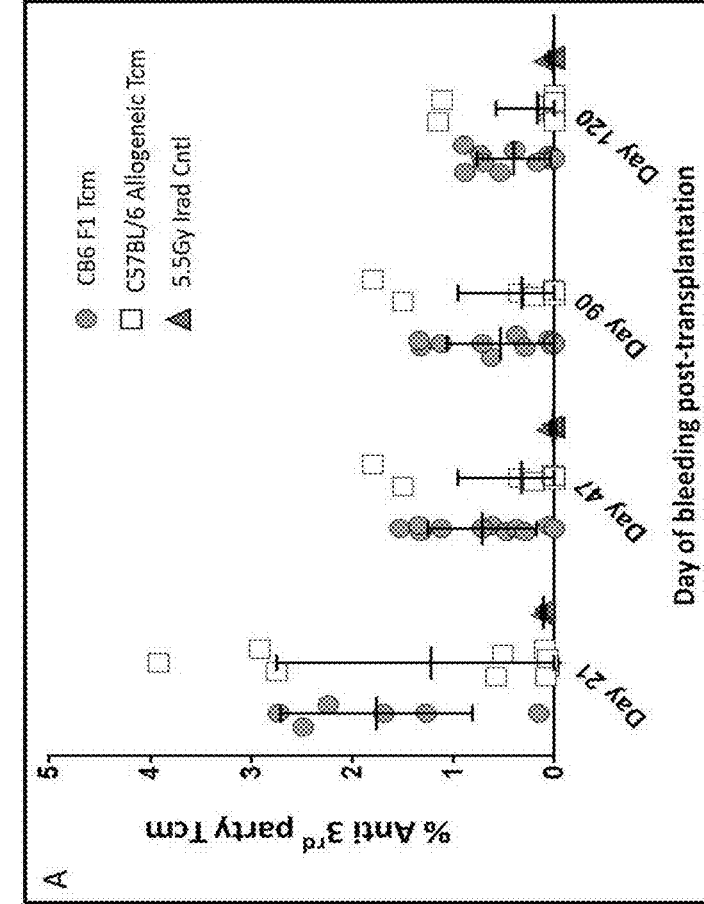

FIGS. 6A-B are graphs illustrating that fully-allogeneic Tcm cells persist in 5.5 Gy Balb/c mice for a prolonged period. Balb/c (H-2$^d$) mice were transplanted as outlined in FIG. 1C. Tcm cells were of CB6-F1 (H-2$^{db}$) or C57BL/6 (H-2$^b$) origin. Mice were bled on the indicated days and the Tcm cell population was analyzed by FACS using $\alpha H2D^d$ (Host) and $\alpha H2K^b$ (Donor) to identify H2$^{db}$F1-Tcm and H2$^b$ Allo-Tcm cells. FIG. 6A is a scatter plot depicting the percentage of Tcm cells in Balb/c hosts. Each dot represents the Tcm cell population in one mouse belonging to the appropriate group, showing the mean and SD of each group. FIG. 6B is a time curve graph illustrating decrease in Tcm cell population in peripheral blood from over a prolonged period of time.

Figure 7:
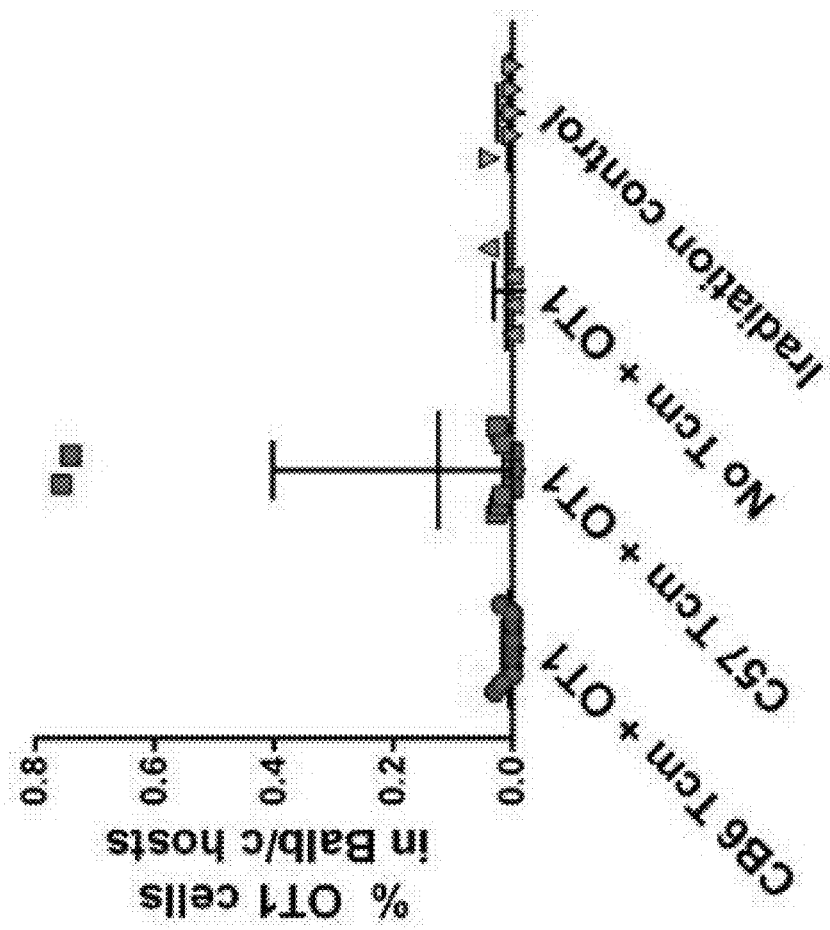

FIG. 7 is a graph illustrating that fully-allogeneic Tcm cells persist in 5.5 Gy Balb/c mice and facilitate engraftment of additional donor T cells. Balb/c (H-2$^d$) mice received 5.5 Gy TBI on day −1, and 5×10$^6$ CB6 (H-2$^{db}$) or C57BL/6(H-2$^b$) derived Tcm cells on day 0. 89 days post Tcm cell injection, the mice were irradiated with 2 Gy TBI, the following day they received 2×10$^6$ CD45.1$^+$, OT1$^+$, RAG$^+$ CD8+ cells. Scatter plot showing bleeding on day 120 post Tcm cell transplantation and 30 days post OT-1 cells transplantation.

Figure 8:
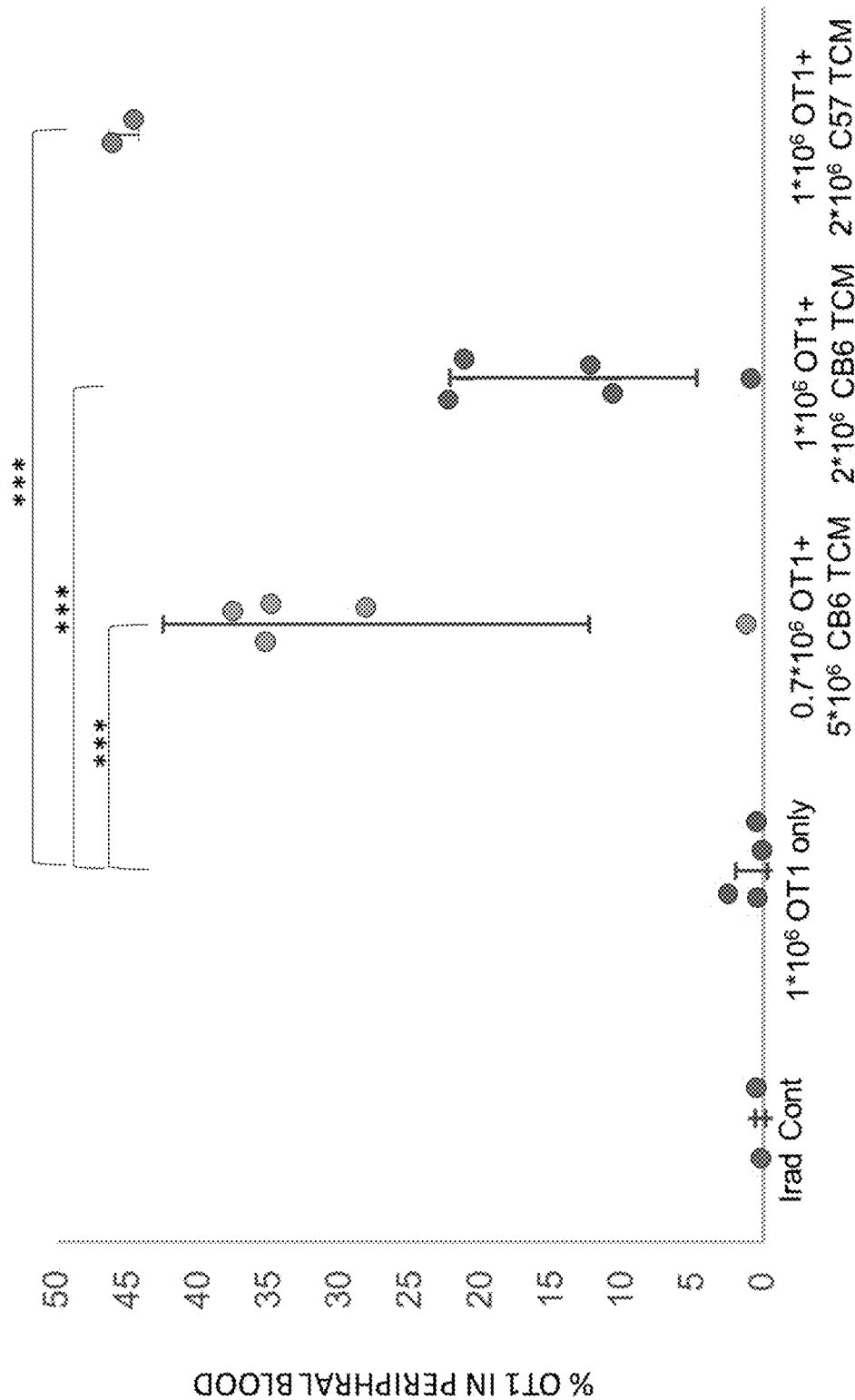

FIG. 8 is a graph illustrating an analysis of OT-1 cells in the peripheral blood of sublethally irradiated Balb/c mice. Balb/c (H-2$^d$) mice received 5.25 Gy TBI on day −1, and proceeded to receive naive CD8$^+$ OT-1$^+$CD45.1$^+$RAG$^-$ cells on day 0, with or without the CB6 (H-2$^{db}$) or C57BL/6 (H-2$^b$) derived Tcm cells at the indicated numbers. Sixty days post Tcm cell injection peripheral blood of the mice was tested to detect the presence of OT-1 cells using FACS analysis. Scatter plot showing the percentage of OT-1 cells of different groups out of the total CD8$^+$H-2$^{b+}$ cells.

Figure 9:
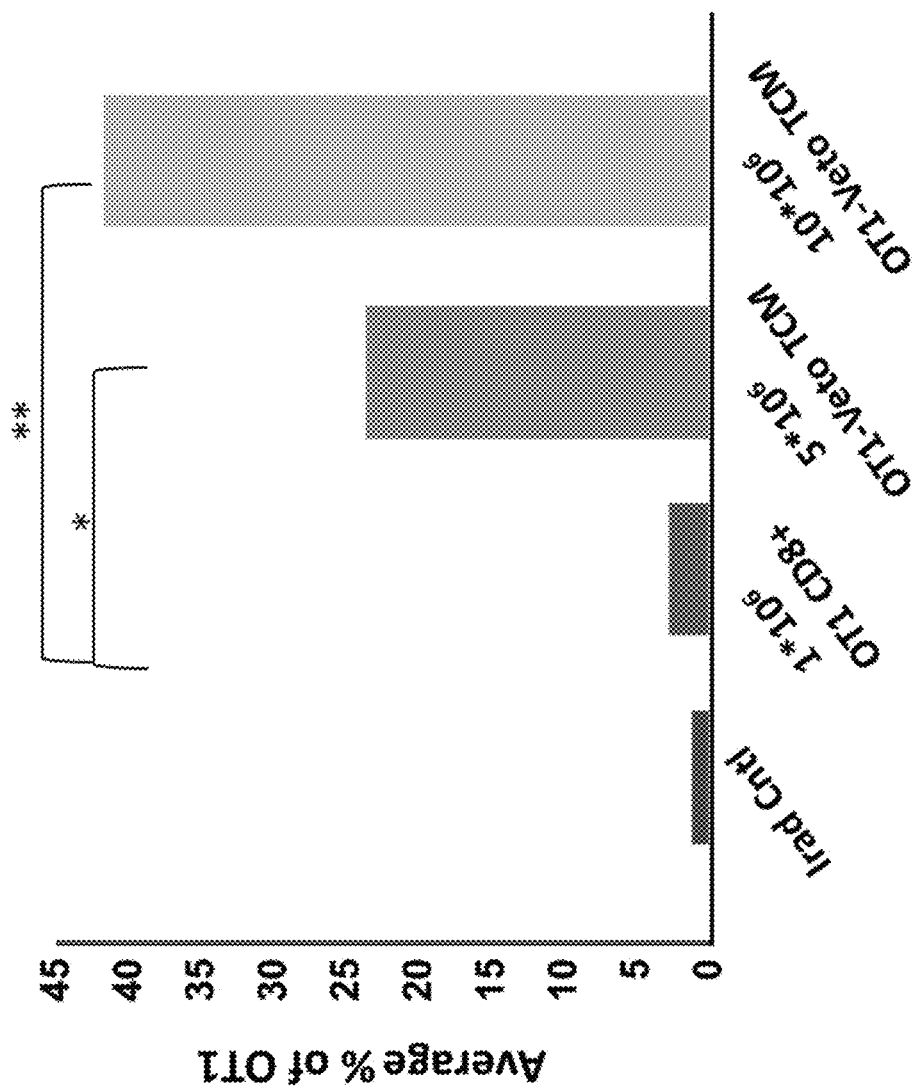

FIG. 9 is a graph illustrating engraftment and survival of Tcm cells prepared from OT-1 mice transplanted in a reduced intensity conditioning Balb/c mouse model.

DESCRIPTION OF SPECIFIC EMBODIMENTS OF THE INVENTION

The present invention, in some embodiments thereof, relates to genetically modified tolerance inducing central memory T-lymphocytes transduced to express a cell surface receptor and, more particularly, but not exclusively, to the use of same in immunotherapy.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cell-based therapies with lymphocytes and antigen-presenting cells are promising approaches for immunotherapy. Adoptive cell transfer (ACT), including transfer of immune-derived cells, from an autologous or non-autologous source offers the goal of transferring the immunologic functionality and characteristics into the host. One method previously employed for ACT comprises genetically modified T cells (e.g. expressing a T cell receptor or a chimeric antigen receptor), wherein the specificity of the cells is redirected towards the target antigen. However, the problem of graft rejection (by the transplant recipient) and/or graft versus host disease (by the transplanted cells) is an ongoing problem that needs to be overcome in order to pursue therapeutic potential of these cells.

While reducing the present invention to practice, the present inventors have uncovered that anti-third party central memory T (Tcm) cells, which are devoid of graft versus host reactivity, are endowed with intrinsic veto tolerance inducing activity and can induce tolerance on their own, in the absence of hematopoietic progenitors. The present inventors further discovered that the anti-third party Tcm cells can be genetically modified to express a T cell receptor (e.g. transgenic T cell receptor or a chimeric antigen receptor) and can be used to combat disease while inducing veto activity and being devoid of graft versus host potential.

As is shown herein below and in the Examples section which follows, the present inventors have shown that allogeneic donor type anti-third party Tcm cells can survive in a host for a prolonged time with or without a concomitant bone marrow transplant (e.g. more than 120 days, FIGS. 2A-B and FIGS. 6A-B, respectively). Moreover, the anti-third party Tcm cells exerted veto activity (FIG. 3). Thus, application of anti-third party Tcm cells alone (i.e. in the absence of BM precursors) offers a useful tool for immunotherapy particularly for targeting tumor antigens, pathogens (e.g. viral antigens) and self-antigens. Thus, these results further substantiate genetically modifying tolerogenic anti-third party Tcm cells, from any cell donor, to express heterologous T cell effector functions, thus resulting in a universal product for immunotherapy targeting a disease antigen and avoiding graft rejection and graft versus host disease (GVHD).

Taken together, these cells offer the solution of being devoid of graft versus host potential, graft rejection and targeting specific antigens all in a single cell. These cells eliminate the need of using autologous cells for treatment or the need of transplanting hematopoietic cells therewith. Moreover, these cells overcome the need of manufacturing the cell based therapies on a "per patient basis" and enable manufacture of an "off-the-shelf" product for therapy.

Thus, according to one aspect of the present invention there is provided an isolated cell having a central memory T-lymphocyte (Tcm) phenotype, the cell being tolerance-inducing cell and capable of homing to the lymph nodes following transplantation, the cell being transduced to express a cell surface receptor comprising a T cell receptor signaling module.

As used herein, the term "isolated cell" refers to a cell which has been separated from its natural environment (e.g. from a tissue e.g. from a human body).

The phrase "central memory T-lymphocyte (Tcm) phenotype" as used herein refers to a subset of T cytotoxic cells which home to the lymph nodes. Cells having the Tcm phenotype, in humans, typically comprise a CD3+/CD8+/CD62L+/CD45RO+/CD45RA− signature. It will be appreciated that Tcm cells may express all of the signature markers on a single cell or may express only part of the signature markers on a single cell.

A Tcm cell typically homes to the lymph nodes following transplantation.

According to some embodiments, the Tcm cell of the present invention may home to any of the lymph nodes following transplantation, as for example, the peripheral lymph nodes and mesenteric lymph nodes. The homing nature of these cells allows them to exert their tolerance effect in a rapid and efficient manner.

The phrase "tolerance inducing cells" as used herein refers to cells which provoke decreased responsiveness of the recipient's cells (e.g. recipient's T cells) when they come in contact with the recipient's cells as compared to the responsiveness of the recipient's cells in the absence of administered tolerance inducing cells. Tolerance inducing cells include veto cells (i.e. T cells which lead to apoptosis of host T cells upon contact with same) as was previously described in PCT Publication Nos. WO 2001/049243 and WO 2002/102971.

According to one embodiment, the Tcm cells of the invention are also non-GVHD inducing cells.

The term "non-GVHD" as used herein refers to having substantially reduced or no graft versus host inducing reactivity. Thus, the cells of the present invention are generated as to not significantly cause graft versus host disease (GVHD) as evidenced by survival, weight and overall appearance of the transplanted subject 30-100 days following transplantation.

According to one embodiment, the cells of the present invention have at least 20%, at least 30%, at least 40%, at least 50%, at least 55%, at least 60%, at least 65%, at least 70%, at least 75%, at least 80%, at least 85%, at least 90%, at least 95% or even 100% reduced reactivity against a host relative to transplantation of T cells which are not anti-third party Tcm cells.

According to one embodiment, the cell of the present invention comprising a Tcm phenotype is genetically modified.

According to one embodiment, the cell of the invention is transduced to express a cell surface receptor comprising a T cell receptor signaling module.

As used herein, the term "transduced" may be interchangeably used with the terms "transfected" or "transformed" and refers to a process by which an exogenous nucleic acid (heterologous) is transferred or introduced into a cell. A "transfected" or "transformed" or "transduced" cell is one which has been transfected, transformed or transduced with exogenous nucleic acid. The cell includes the primary cell and its progeny, or cell lines thereof.

The term "cell surface receptor" as used herein refers to a recombinant or synthetic molecule presented on a cell membrane which binds to a ligand (e.g. an antigen) and mediates activation of the cell.

The term "antigen" or "Ag" as used herein is defined as a molecule that provokes an immune response. The skilled artisan will understand that any macromolecule, including virtually all proteins or peptides, as well as carbohydrates, lipids and DNA can serve as an antigen.

According to some embodiments of the invention, the antigen is associated with a malignant disease, i.e. tumor antigen (e.g., tumor specific antigen or a tumor associated antigen), a viral protein antigen, a bacterial protein antigen, a fungal protein antigen, antigens associated with an allergic reaction (i.e. allergic antigens) or an autoimmune associated antigen (e.g., a "self" antigen), as described in further detail hereinbelow.

The cell surface receptor of the invention comprises a T cell receptor signaling module.

The term "T cell receptor signaling module" refers to an intracellular portion of the receptor responsible for activation of at least one of the normal effector functions of the T cell in which the receptor has been placed in. Normal effector functions of a T cell may include, for example, secretion of immunostimulatory cytokines (e.g. IFN-gamma, IL-2, TNF-alpha), antigen specific cytotoxicity, and cell proliferation. Thus, the T cell receptor signaling module of the invention refers to the portion of a protein which transduces the effector function signal and directs the cell to perform a specialized function.

According to one embodiment, the cell surface receptor comprises a transgenic T cell receptor (tg-TCR) or a chimeric antigen receptor (CAR).

As used herein, the term "transgenic T cell receptor" or "tg-TCR" refers to a recombinant or synthetic molecule comprising the specificity of a T cell receptor (TCR), i.e. recognition of antigenic peptides (i.e. antigen) presented by major histocompatability complex (MHC) proteins.

The tg-TCR of the invention typically comprises two chains (i.e., polypeptide chains), such as, an alpha chain of a T cell receptor (TCR), a beta chain of a TCR, a gamma chain of a TCR, a delta chain of a TCR, or a combination thereof (e.g. αβ chains or γδ chains). The polypeptides of the tg-TCR can comprise any amino acid sequence, provided that the tg-TCR has antigenic specificity and T cell effector functions as described hereinabove. It will be appreciated that antigen specificity is determined by the TCR heterodimer (i.e. by the αβ or γδ chains).

It will be appreciated that each of the two chains is typically composed of two extracellular domains, i.e. the variable (V) region and the constant (C) region.

According to one embodiment, the tg-TCR comprises the variable regions of a TCR. According to a specific embodiment, the tg-TCR comprises the variable regions of α- and β-chains of a TCR. According to another specific embodiment, the tg-TCR comprises the variable regions of γ- and δ-chains of a TCR.

According to some embodiments of the invention, the variable region of the tg-TCR comprises complementarity determining regions (CDRs) which are capable of specifically binding the antigen. The CDRs may be selected from any of CDR1, CDR2, CDR3 and/or CDR4. According to a specific embodiment, the CDRs are present on a single chain, preferably the CDRs are present on both chains of the tg-TCR.

According to one embodiment, the tg-TCR comprises the constant regions of a TCR. According to a specific embodiment, the tg-TCR comprises the constant regions of α- and β-chains of a TCR. According to another specific embodiment, the tg-TCR comprises the constant regions of γ- and δ-chains of a TCR.

In order to avoid formation of mixed dimmers between endogenous TCRs (i.e. TCRs originating within the transduced cell) and the tg-TCR chains, the tg-TCR of the invention may comprise the constant region a murine (e.g. mouse) TCR. Another approach which may be used to increase the specific pairing of tg-TCR chains is to introduce additional cysteine residues within the constant region of the tg-TCR chains (e.g. α and β chains), this results in formation of an additional disulfide bond. Alternatively, mutational inversions of the critical interacting amino acids in the tg-TCR chain (e.g. α and β chain) constant regions may be introduced which favor the pairing of the tg-TCR chains and also increase tg-TCR reactivity. Alternatively or additionally, downregulation of the endogenous TCR may be implemented using, for example, small interfering RNA (siRNA) which is used to specifically down-regulate the endogenous TCR. For further details, see e.g. Zhang and Morgan, Adv Drug Deliv Rev. (2012) 64(8): 756-762, incorporated herein by reference.

As mentioned, the tg-TCR recognizes an antigen in an MHC dependent manner.

As used herein the phrase "major histocompatibility complex" or "MHC" refers to a complex of antigens encoded by a group of linked loci, which are collectively termed H-2 in the mouse and human leukocyte antigen (HLA) in humans. The two principal classes of the MHC antigens, class I and class II, each comprise a set of cell surface glycoproteins which play a role in determining tissue type and transplant compatibility.

The main MHC class I molecules are contemplated herein.

Major histocompatibility complex (MHC) class I molecules are expressed on the surface of nearly all cells. These molecules function in presenting peptides which are mainly derived from endogenously synthesized proteins to CD8+ T cells via an interaction with the αβ T-cell receptor. In humans, there are several MHC haplotypes, such as, for example, HLA-A2, HLA-A1, HLA-A3, HLA-A24, HLA-A28, HLA-A31, HLA-A33, HLA-A34, HLA-B7, HLA-B45 and HLA-Cw8, their sequences can be found at the kabbat data base, at www(dot)immuno(dot)bme(dot)nwu(dot)edu.

Further information concerning MHC haplotypes can be found in Paul, B. Fundamental Immunology Lippincott-Raven Press.

The choice of tg-TCR depends upon the type and number of antigens that define the surface of a target cell. For example, the tg-TCR may be chosen to recognize an antigen that acts as a cell surface marker on a target cell associated with a particular disease state. Thus, for example, cell surface markers that may act as antigens for recognition by the tg-TCR may include those associated with viral, bacterial and parasitic infections, autoimmune disease and cancer cells. Examples are provided below.

To generate a successful tg-TCR, an appropriate target sequence needs to first be identified. Accordingly, a TCR may be isolated from an antigen reactive T cell (e.g. tumor reactive T cell) or, where this is not possible, alternative technologies can be employed. According to an exemplary embodiment, a transgenic animal (e.g. rabbit or mouse, preferably a human-HLA transgenic mouse) is immunized with human antigen peptides (e.g. tumor or viral antigens) to generate T cells expressing TCRs against the human antigens [as described e.g. in Stanislawski et al., Nat Immunol. (2001) 2(10):962-70]. According to another exemplary embodiment, antigen-specific T cells (e.g. tumor specific T cells) are isolated from a patient experiencing disease (e.g. tumor) remission and the reactive TCR sequences are isolated therefrom [as described e.g. in de Witte et al., Blood (2006) 108(3):870].

According to another exemplary embodiment, in vitro technologies are employed to alter the sequence of an existing TCR to enhance the avidity of a weakly reactive antigen-specific TCR with a target antigen (such methods are described below).

According to one embodiment, the tg-TCR of the invention is selected to recognize the antigen peptide-HLA complex with high avidity (i.e. the physical strength of the monomeric interaction between the TCR and a peptide-MHC-complex).

Producing cells with high functional avidity (i.e. that which effectively respond to antigens) can be achieved using any method known to one of ordinary skill in the art. Thus, according to one example, increasing the avidity of the tg-TCR is attained by increasing the affinity (i.e. strength of binding of a TCR to its ligand) of the tg-TCR or increasing the expression of the tg-TCR on the cell surface. According to one exemplary embodiment, increasing the TCR affinity is carried out by modification of tg-TCR genes. For example, one possible modification of the tg-TCR genes includes modifications to a complementarity determining region (CDR), e.g. third CDR (CDR3), of the tg-TCR. Accordingly, single or dual amino acid substitutions in the CDR chains (e.g. α or β chains) may be utilized in order to increase affinity of the tg-TCR and to enhance antigen-specific reactivity in transduced cells. According to another exemplary embodiment, increasing the functional avidity of tg-TCR is carried out by the removal of defined N-glycosylation motifs in the constant domains of tg-TCR chains. According to another exemplary embodiment, increasing the affinity is carried out by codon optimization.

Accordingly, rare codons of the tg-TCR are replaced by codons most frequently distributed in highly expressed human genes. During the optimization process cis-acting AT or GC rich sequence stretches, cryptic splicing and RNA instability motifs may also be removed. For further information, see e.g. Zhang and Morgan, Adv Drug Deliv Rev. (2012), supra, incorporated herein by reference.

According to one embodiment, the signaling module of the tg-TCR may comprise a single subunit or a plurality of signaling units. Accordingly, the tg-TCR of the invention may use co-receptors that act in concert with a TCR to initiate signal transduction following antigen receptor engagement, as well as any derivative or variant of thereof having the same functional capability.

According to one embodiment, the TCR signaling module comprises the CD3 complex (e.g. CD3 chains, e.g. CD3δ/ε, CD3γ/ε and/or zeta chains, e.g. ζ/ζ or ζ/η).

Additionally or alternatively, the TCR signaling module may comprise co-stimulatory protein receptors to provide additional signals to the T cell. These are discussed in detail hereinbelow.

According to one embodiment, the tg-TCR may comprise a transmembrane domain as described in detail hereinbelow.

Methods of transducing a cell with a TCR are described in detail hereinbelow.

As used herein the phrase "chimeric antigen receptor (CAR)" refers to a recombinant or synthetic molecule which combines specificity for a desired antigen with a T cell receptor-activating intracellular domain (i.e. T cell receptor signaling module) to generate a chimeric protein that exhibits cellular immune activity to the specific antigen.

Thus, the CAR of the invention generally comprises an extracellular domain comprising an antigen binding moiety, a transmembrane domain and an intracellular domain (i.e. the cytoplasmic domain) that is required for an efficient response of the T cell to the antigen.

Antigen Binding Moiety

In one embodiment, the CAR of the invention comprises a target-specific binding element otherwise referred to as an antigen binding moiety. The choice of moiety depends upon the type and number of ligands (i.e. antigens) that define the surface of a target cell. For example, the antigen binding domain may be chosen to recognize a ligand (i.e. antigen) that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

According to some embodiments of the invention, the antibody binding moiety comprises complementarity determining regions (CDRs) which are capable of specifically binding the antigen. Such CDRs can be obtained from an antibody.

The term "antibody" as used in this invention includes intact molecules as well as functional fragments thereof, such as Fab, Fab', F(ab')2, Fv, linear antibodies, scFv antibodies, and multispecific antibodies formed from antibody fragments that are capable of binding to the antigen. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; (6) CDR peptide is a peptide coding for a single complementarity-determining region (CDR); and (7) Single domain antibodies (also called nanobodies), a genetically engineered single monomeric variable antibody domain which selectively binds to a specific antigen. Nanobodies have a molecular weight of only 12-15 kDa, which is much smaller than a common antibody (150-160 kDa).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. Kappa- and lambda-light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Once the CDRs of an antibody are identified, using conventional genetic engineering techniques, expressible polynucleotides encoding any of the forms or fragments of antibodies described herein can be synthesized and modified in one of many ways in order to produce a spectrum of related-products.

According to some embodiments of the invention, the CDRs are derived from αβ T cell receptor (TCR) which specifically binds to the antigen.

According to some embodiments of the invention, the CDRs are derived from γδ T cell receptor (TCR) which specifically binds to the antigen.

According to some embodiments of the invention, the CDRs are derived from an engineered affinity-enhanced αβ T cell receptor or γδ T cell receptor (TCR) which specifically binds to the antigen (as discussed in detail hereinabove).

According to some embodiments of the invention, the CDRs are derived from an engineered αβ T cell receptor or γδ T cell receptor (TCR) with improved stability or any other biophysical property.

According to some embodiments of the invention, the CDRs are derived from a T cell receptor-like (TCRLs) antibody which specifically binds to the antigen. Examples of TCRLs and methods of generating same are described in WO03/068201, WO2008/120203, WO2012/007950, WO2009125395, WO2009/125394, each of which is fully incorporated herein by their entirety.

According to some embodiments of the invention, the antigen binding domain comprises a single chain Fv (scFv) molecule.

Cytoplasmic Domain

The cytoplasmic domain (also referred to as "intracellular signaling domain" or "T cell receptor signaling module") of the CAR molecule of the invention is responsible for activation of at least one of the normal effector functions of the cell in which the CAR has been placed in.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR molecule of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs (ITAMs).

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A co-stimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with 4-1BB as the co-stimulatory signaling element, other costimulatory elements are within the scope of the invention.

According to some embodiments of the invention, the intracellular domain comprises a co-stimulatory signaling region and a zeta chain portion. The co-stimulatory signaling region refers to a portion of the CAR molecule comprising the intracellular domain of a co-stimulatory molecule. Co-stimulatory molecules are cell surface molecules other than antigen receptors or their ligands that are required for an efficient response of lymphocytes to antigen.

"Co-stimulatory ligand," as the term is used herein, includes a molecule on an antigen presenting cell [e.g., an aAPC (artificial antigen presenting cell), dendritic cell, B cell, and the like] that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or down regulation of key molecules.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter cilia, a MHC Class I molecule loaded with a peptide, an anti-CD3 antibody, a superagonist anti-CD28 antibody, and a superagonist anti-CD2 antibody.

With respect to the cytoplasmic domain, the CAR molecule of some embodiments of the invention can be designed to comprise the CD28 and/or 4-1BB signaling domain by itself or be combined with any other desired cytoplasmic domain(s) useful in the context of the CAR molecule of some embodiments of the invention. In one embodiment, the cytoplasmic domain of the CAR can be designed to further comprise the signaling domain of CD3-zeta. For example, the cytoplasmic domain of the CAR can include but is not limited to CD3-zeta, 4-1BB and CD28 signaling modules and combinations thereof.

According to some embodiments of the invention, the intracellular domain comprises at least one, e.g., at least two, at least three, at least four, at least five, e.g., at least six of the polypeptides selected from the group consisting of: CD3ζ (CD247, CD3z), CD27, CD28, 4-1BB/CD137, ICOS, OX40/CD134, DAP10, tumor necrosis factor receptor (TNFr) and Lsk.

According to some embodiments of the invention, the intracellular domain comprises the CD3-chain [CD247 molecule, also known as "CD3-ZETA" and "CD3z"; GenBank Accession NOs. NP_000725.1 and NP_932170.1], which is the primary transmitter of signals from endogenous TCRs.

According to some embodiments of the invention, the intracellular domain comprises various co-stimulatory protein receptors to the cytoplasmic tail of the CAR to provide additional signals to the T cell ("second generation" CAR). Examples include, but are not limited to, CD28 [e.g., GenBank Accession Nos. NP_001230006.1, NP_001230007.1, NP_006130.1], 4-1BB [tumor necrosis factor receptor superfamily, member 9 (TNFRSF9), also known as "CD137", e.g., GenBank Accession No. NP_001552.2], ICOS [inducible T-cell co-stimulator, e.g., GenBank Accession No. NP_036224.1], DAP10 [hematopoietic cell signal transducer, e.g., GenBank Accession Nos. NP_001007470, NP_055081.1] and Lsk [LCK proto-oncogene, Src family tyrosine kinase, e.g., GenBank Accession Nos. NP_001036236.1, NP_005347.3]. Preclinical studies have indicated that the "second generation of CAR designs improves the antitumor activity of T cells.

According to some embodiments of the invention, the intracellular domain comprises multiple signaling domains, such as CD3z-CD28-4-1BB or CD3z-CD28-OX40, to further augment potency. The term "OX40" refers to the tumor necrosis factor receptor superfamily, member 4 (TNFRSF4), e.g., GenBank Accession No. NP_003318.1 ("third-generation" CARs).

According to some embodiments of the invention, the intracellular domain comprises CD28-CD3z, CD3z, CD28-CD137-CD3z. The term "CD137" refers to tumor necrosis factor receptor superfamily, member 9 (TNFRSF9), e.g., GenBank Accession No. NP_001552.2.

According to some embodiments of the invention, the intracellular domain comprises CD3z, CD28 and a tumor necrosis factor receptor (TNFr).

According to some embodiments of the invention, the CAR comprises a CD3 zeta chain.

According to some embodiments of the invention, the CAR comprises at least one co-stimulatory domain selected from the group consisting of CD28, CD134/OX40, CD137/4-1BB, Lck, ICOS and DAP10.

According to some embodiments of the invention, the CAR comprises at least two co-stimulatory domains selected from the group consisting of CD28, CD134/OX40, CD137/4-1BB, Lck, ICOS and DAP10.

Transmembrane Domain

The transmembrane domain of the CAR may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

According to some embodiments of the invention, the transmembrane domain comprised in the CAR molecule of some embodiments of the invention is a transmembrane domain that is naturally associated with one of the domains in the CAR. According to some embodiments of the invention, the transmembrane domain can be selected or modified by amino acid substitution to avoid binding of such domains to the transmembrane domains of the same or different surface membrane proteins to minimize interactions with other members of the receptor complex.

According to some embodiments of the invention, the transmembrane domain is the CD8α hinge domain.

According to some embodiments, between the extracellular domain and the transmembrane domain of the CAR molecule, or between the cytoplasmic domain and the transmembrane domain of the CAR molecule, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

As mentioned, the cell surface receptor of the cell of the invention (e.g. tg-TCR and/or CAR) binds to an antigen (e.g. on a target cell).

According to one embodiment, the antigen may comprise a tumor associated antigen, a viral antigen, a bacterial antigen, a fungal antigen, a protozoa antigen, a parasite antigen, an allergy associated antigen and/or an autoimmune antigen.

As used herein the phrase "tumor antigen" refers to an antigen that is common to specific hyperproliferative disorders such as cancer. Tumor antigens are proteins that are produced by tumor cells that elicit an immune response, particularly T-cell mediated immune responses. The selection of the antigen binding moiety of the invention will depend on the particular type of cancer to be treated.

According to one embodiment, the tumor antigen is associated with a solid tumor.

According to one embodiment, the tumor antigen is associated with a hematologic malignancy.

The type of tumor antigen referred to in the invention includes a tumor-specific antigen (TSA) or a tumor-associated antigen (TAA). A "TSA" refers to a protein or polypeptide antigen unique to tumor cells and which does not occur on other cells in the body. A "TAA" refers to a protein or polypeptide antigen that is expressed by a tumor cell. For example, a TAA may be one or more surface proteins or polypeptides, nuclear proteins or glycoproteins, or fragments thereof, of a tumor cell.

The antigens discussed herein are merely included by way of example. The list is not intended to be exclusive and further examples will be readily apparent to those of skill in the art.

Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

Non-limiting examples of TSA or TAA antigens include the following: Differentiation antigens such as MART-1/MelanA (MART-1), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.291\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90 \Mac-2 binding protein\cyclophilin C-associated protein, TAAL6, TAG72, TLP, and TPS.

Further examples of tumor antigens include, but are not limited to, A33, BAGE, Bcl-2, β-catenin, CA125, CA19-9, CD5, CD19, CD20, CD21, CD22, CD33, CD37, CD45, CD123, CEA, c-Met, CS-1, cyclin B1, DAGE, EBNA, EGFR, ephrinB2, estrogen receptor, FAP, ferritin, folate-binding protein, GAGE, G250, GD-2, GM2, gp75, gp100 (Pmel 17), HER-2/neu, HPV E6, HPV E7, Ki-67, LRP, mesothelin, p53 and PRAME. Further tumor antigens are provided in van der Bruggen P, Stroobant V, Vigneron N, Van den Eynde B. Peptide database: T cell-defined tumor antigens. *Cancer Immun* (2013), www(dot)cancerimmunity (dot)org/peptide/, incorporated herein by reference.

According to a specific embodiment, the tumor antigen includes, but is not limited to, CD19, CD20, CD22, ROR1, Mesothelin, CD33/IL3Ra, c-Met, PSMA, Glycolipid F77, EGFRvIII, Her2, GD-2, gp100, p53, carcinoembryonic antigen (CEA), MY-ESO-1, MART-1, MAGE A3, and the like.

According to one embodiment, the target antigen is CD19.

According to some embodiments of the invention, the antigen is a viral antigen. The viral antigen may be derived from any virus, such as but not limited to, human immunodeficiency virus (HIV), influenza, Cytomegalovirus (CMV), T-cell leukemia virus type 1 (TAX), hepatitis C virus (HCV), (HBV), Epstein-Barr virus (EBV), Adenovirus (Adv), cold viruses, flu viruses, hepatitis A, B, and C viruses, herpes simplex, Japanese encephalitis, measles, polio, rabies, respiratory syncytial, rubella, smallpox, varicella zoster, rotavirus, West Nile virus, Polyomavirus (e.g. BK virus) and/or zika virus.

According to some embodiments of the invention, the viral antigens include, but are not limited to, viral epitopes from a polypeptide selected from the group consisting of: human T cell lymphotropic virus type I (HTLV-1) transcription factor (TAX), influenza matrix protein epitope, Epstein-Bar virus (EBV)-derived epitope, HIV-1 RT, HIV Gag, HIV Pol, influenza membrane protein M1, influenza hemagglutinin, influenza neuraminidase, influenza nucleoprotein, influenza nucleoprotein, influenza matrix protein (M1), influenza ion channel (M2), influenza non-structural protein NS-1, influenza non-structural protein NS-2, influenza PA, influenza PB1, influenza PB2, influenza BM2 protein, influenza NB protein, influenza nucleocapsid protein, Cytomegalovirus (CMV) phosphorylated matrix protein (pp65), TAX, hepatitis C virus (HCV), HBV pre-S protein 85-66, HTLV-1 tax 11-19, HBV surface antigen 185-194.

According to some embodiments of the invention, the antigen is a bacterial antigen. The bacterial antigen may be derived from any bacteria, such as but not limited to, anthrax; gram-negative bacilli, *chlamydia, diptheria, haemophilus influenza, Helicobacter pylori, malaria, Mycobacterium tuberculosis, pertussis* toxin, pneumococcus, rickettsiae, *staphylococcus, streptococcus* and tetanus.

According to some embodiments of the invention, the bacterial antigens include, but are not limited to, anthrax antigens include, but are not limited to, anthrax protective antigen; gram-negative bacilli antigens include, but are not limited to, lipopolysaccharides; *haemophilus influenza* antigens include, but are not limited to, capsular polysaccharides; *diptheria* antigens include, but are not limited to, diptheria toxin; *Mycobacterium tuberculosis* antigens include, but are not limited to, mycolic acid, heat shock protein 65 (HSP65), the 30 kDa major secreted protein and antigen 85A; *pertussis* toxin antigens include, but are not limited to, hemagglutinin, pertactin, FIM2, FIM3 and adenylate cyclase; pneumococcal antigens include, but are not limited to, pneumolysin and pneumococcal capsular polysaccharides; rickettsiae antigens include, but are not limited to, rompA; streptococcal antigens include, but are not limited to, M proteins; and tetanus antigens include, but are not limited to, tetanus toxin.

According to some embodiments of the invention, the antigen is a superbug antigen (e.g. multi-drug resistant bacteria). Examples of superbugs include, but are not limited to, *Enterococcus faecium, Clostridium difficile, Acinetobacter baumannii, Pseudomonas aeruginosa*, and Enterobacteriaceae (including *Escherichia coli, Klebsiella pneumoniae, Enterobacter* spp.).

According to some embodiments of the invention, the antigen is a fungal antigen. Examples of fungi include, but are not limited to, *candida, coccidiodes, cryptococcus, histoplasma, leishmania, plasmodium*, protozoa, parasites, schistosomae, tinea, *toxoplasma*, and *Trypanosoma cruzi*.

According to some embodiments of the invention, the fungal antigens include, but are not limited to, coccidiodes antigens include, but are not limited to, spherule antigens; cryptococcal antigens include, but are not limited to, capsular polysaccharides; *histoplasma* antigens include, but are not limited to, heat shock protein 60 (HSP60); *leishmania* antigens include, but are not limited to, gp63 and lipophosphoglycan; *Plasmodium falciparum* antigens include, but are not limited to, merozoite surface antigens, sporozoite surface antigens, circumsporozoite antigens, gametocyte/gamete surface antigens, protozoal and other parasitic antigens including the blood-stage antigen pf 155/RESA; schistosomae antigens include, but are not limited to, glutathione-S-transferase and paramyosin; tinea fungal antigens include, but are not limited to, trichophytin; *toxoplasma* antigens include, but are not limited to, SAG-1 and p30; and *Trypanosoma cruzi* antigens include, but are not limited to, the 75-77 kDa antigen and the 56 kDa antigen.

According to some embodiments of the invention, the antigen is an antigen expressed by cells associated with an allergic condition. Examples of allergic antigens include, but are not limited to, pollen antigens such as Japanese cedar pollen antigens, ragweed pollen antigens, rye grass pollen antigens, animal derived antigens (such as dust mite antigens and feline antigens), histocompatibility antigens, and penicillin and other therapeutic drugs.

According to some embodiments of the invention, the antigen is an autoantigen associated with an autoimmune disease.

The term "autoimmune disease" as used herein is defined as a disorder that results from an autoimmune response. An autoimmune disease is the result of an inappropriately excessive response to a self-antigen.

Examples of autoimmune diseases include, but are not limited to, Addison's disease, alopecia greata, ankylosing spondylitis, autoimmune hepatitis, autoimmune parotitis, Crohn's disease, inflammatory bowel disease (IBD), Celiac disease, dermatitis (including atopic dermatitis and eczematous dermatitis), type I diabetes, dystrophic epidermolysis bullosa, epididymitis, glomerulonephritis, Graves' disease, Guillain-Barr syndrome, Hashimoto's disease, hemolytic anemia, systemic lupus erythematosus (SLE), multiple sclerosis (MS), myasthenia gravis, pemphigus vulgaris, psoriasis, rheumatic fever, arthritis (including rheumatoid arthritis, juvenile rheumatoid arthritis, osteoarthritis, psoriatic arthritis), sarcoidosis, scleroderma, Sjogren's syndrome, Stevens-Johnson syndrome, Wegener's granulomatosis, spondyloarthropathies, thyroiditis, vasculitis, vitiligo, myxedema, anemia, asthma, pernicious anemia, ulcerative colitis, and stroke, among others.

As used herein the phrase "autoantigenic peptide" refers to an antigen derived from an endogenous (i.e., self protein) or a consumed protein (e.g., by food) against which an inflammatory response is elicited as part of an autoimmune inflammatory response.

It should be noted that the phrases "endogenous", "self" are relative expressions referring to the individual in which the autoimmune response is elicited.

Autoantigens comprise, but are not limited to, cellular proteins, phosphoproteins, cellular surface proteins, cellular lipids, nucleic acids, glycoproteins, including cell surface receptors.

According to some embodiments of the invention the autoantigenic peptide is associated with a disease selected from the group consisting of diabetes, multiple sclerosis, rheumatoid arthritis, celiac disease and stroke.

Multiple sclerosis autoantigens include, but are not limited to, myelin proteins such as myelin basic protein (MBP), proteolipid protein (PLP), and myelin oligodendrocyte glycoprotein (MOG).

Rheumatoid arthritis-associated autoantigens include, but are not limited to, autoantigenic peptides derived from Collagen II (COL2A1), Matrix metalloproteinase-1 (MMP1), Aggrecan Core Protein Precursor (ACAN), Matrix Metalloproteinase-16 (MMP16), Tenascin (TNXB) and Heterogeneous Nuclear Ribonucleoprotein A2 (HNRNPA2B1).

Type 1 Diabetes (T1D) autoantigens include, but are not limited to, antigens expressed in the pancreatic islets, including glutamic acid decarboxylase (GAD65) and beta-cell autoantigenic peptide.

Celiac (Coeliac) autoantigens include, but are not limited to, gliadin (e.g. alpha Gliadin, gamma Gliadin) and Heat shock protein 20.

Crohn's disease, Ulcerative Colitis or Inflammatory bowel disease (IBD), autoantigens include, but are not limited to, FAM84A, granule membrane glycoprotein 2 (GP2), CUB And Zona Pellucida-Like Domains 1 (CUZD1), complement C3, catalase and alpha-enolase.

According to some embodiments of the invention, the stroke-associated autoantigens include, but are not limited to, autoantigenic peptides derived from a brain antigen such as myelin basic protein, neurofilaments and the NR2A/2B subtype of the N-methyl-D-aspartate receptor (MOG-35-55).

According to an aspect of some embodiments of the invention there is provided a method of generating the isolated cell of some embodiments of the invention, the method comprising transducing a cell having a central memory T-lymphocyte (Tcm) phenotype, the cell being tolerance-inducing cell and capable of homing to the lymph nodes following transplantation, with a polynucleotide encoding a cell surface receptor comprising a T cell receptor signaling module.

According to one embodiment, the cell having the central memory T-lymphocyte (Tcm) phenotype, being a tolerance-inducing cell and capable of homing to the lymph nodes following transplantation is an anti-third party cell.

The phrase "anti-third party cell" as used herein refers to lymphocytes (i.e. T lymphocyte) which is directed (i.e. by T cell recognition) against a third party antigen or antigens.

As used herein the phrase "third party antigen or antigens" refers to a soluble or non-soluble (such as membrane associated) antigen or antigens which are not present in either the donor or recipient, as depicted in detail infra.

For example, the third party antigens can be third party cells, cell antigens (e.g. cell surface antigens), antigens of viruses (i.e. viral antigen), such as for example, Epstein-Barr virus (EBV) or cytomegalovirus (CMV), or antigens of bacteria (i.e. bacterial antigen), such as flagellin. Viral or bacterial antigens can be presented by cells (e.g., cell line) infected therewith or otherwise made to express viral/bacterial proteins.

Autologous or non-autologous antigen presenting cells, or artificial vehicle or artificial antigen presenting cells, can be used to present short synthetic peptides fused or loaded thereto or to present protein extracts or purified proteins. Such short peptides, protein extracts or purified proteins may be viral or bacterial derived peptides or peptides representing any other antigen.

Dedicated software can be used to analyze viral or other sequences to identify immunogenic short peptides, i.e., peptides presentable in context of class I MHC or class II MHC.

Third party cells can be either allogeneic or xenogeneic with respects to the recipient (explained in further detail hereinbelow). In the case of allogeneic third party cells, such cells have HLA antigens different from that of the donor but which are not cross reactive with the recipient HLA antigens, such that anti-third party cells generated against such cells are not reactive against a transplant or recipient antigens.

According to an embodiment of the present invention the allogeneic or xenogeneic third party cells are stimulatory cells selected from the group consisting of cells purified from peripheral blood lymphocytes (PBL), spleen or lymph nodes, cytokine-mobilized PBLs, in vitro expanded antigen-presenting cells (APC), in vitro expanded dendritic cells (DC) and artificial antigen presenting cells.

The artificial APC of the present invention may be engineered to exhibit autologous MHC with a $3^{rd}$ party peptide or a $3^{rd}$ party MHC without being pulsed with an exogenous peptide. Thus, according to one embodiment, the artificial APC comprises K562 tumor cells transfected with a third party MHC determinant and a co-stimulatory molecule [as previously described e.g. Suhoski M M et al., Mol Ther. (2007) 15(5): 981-8], or fibroblasts transfected with same.

Third party antigens can be presented on the cellular, viral or bacterial surfaces or derived and/or purified therefrom. Additionally, a viral or bacterial antigen can be displayed on an infected cell and a cellular antigen can be displayed on an artificial vehicle such as a liposome or an artificial antigen presenting cell (e.g. leukemic or fibroblast cell line transfected with the third party antigen or antigens).

The third party antigen may further comprise a synthetic peptide presented by autologous presenting cells, non-autologous presenting cells or on an artificial vehicle or on artificial antigen presenting cells.

In addition, third party antigens can, for example, be proteins extracted or purified from a variety of sources. An example of a purified protein which can serve as a third party antigen according to the present invention is ovalbumin. Other examples are envisaged.

Utilizing cells, virally infected cells, bacteria infected cells, viral peptides presenting cells or bacteria peptides presenting cells as third party antigens is particularly advantageous since such third party antigens include a diverse array of antigenic determinants and as such direct the formation of anti-third party cells of a diverse population, which may further serve in faster reconstitution of T-cells in cases where such reconstitution is required, e.g., following lethal or sublethal irradiation or chemotherapy procedure.

Furthermore, when anti-third party cells are directed against third party antigens, the cells are endowed with anti-disease activity. The term "anti-disease activity" refers to the activity (e.g. killing capability) of the Tcm cells against a diseased cell (e.g. cancer cell, such as graft versus leukemia, GVL, activity). This activity is typically due to TCR independent killing mediated by LFA1-I/CAM1 binding [Arditti et al., Blood (2005) 105(8):3365-71. Epub 2004 Jul. 6].

According to one embodiment, the third party cells comprise dendritic cells.

According to one embodiment, the third party cells comprise mature dendritic cells.

Methods of generating third party dendritic cells, which may be used as stimulatory cells for inducing Tcm cells, are well known in the art. Thus, as a non-limiting example, peripheral blood mononuclear cells (PBMC) may be obtained from a third party non-syngeneic cell donor [e.g. in case the Tcm cells are syngeneic, e.g. autologous, the dendritic cells (DCs) may be non-syngeneic, e.g. allogeneic, with respect to the subject; whereas if the Tcm cells are non-syngeneic, e.g. allogeneic, the DCs are selected from a donor being non-syngeneic, e.g. allogeneic, and HLA mismatched with both the subject and the Tcm cells]. Monocytes may then be isolated by plastic adherence and cultured (e.g. in cell culture plates) using DC cell medium (e.g. Cellgro DC medium) supplemented with human serum (e.g. 1% human serum), penicillin/streptomycin and GM-CSF (e.g. 800 IU/ml) and IL-4 (e.g. 20 ng/ml) (available from e.g.

Peprotech, Hamburg, Germany). After about 24-72 h (e.g. 48 h) of culture, DC medium may be added comprising GM-CSF (e.g. 1600 IU/ml) and IL-4 (e.g. 20 ng/ml). About 12-36 h (e.g. 24 h) later, non-adherent cells may be harvested, and large cells (mostly immature DC) may be resuspended in fresh medium containing GM-CSF (e.g. 800 IU/ml), IL-4 (e.g. 20 ng/ml), LPS (e.g. from *E. coli* 055:B5 at e.g. 10 ng/ml) and IFNγ (e.g. 100 IU/ml) (available from e.g. Peprotech, Hamburg, Germany), plated and incubated overnight. The next day, non-adherent cells may be discarded, and adherent DCs may be gently removed using e.g. cold PBS/1% HS after incubation on ice for about 15-30 minutes (e.g. 20 minutes), thereby obtaining large cells consisting of mature DC.

According to one embodiment, the third party cells comprise irradiated dendritic cells.

Thus, according to one embodiment, the DCs are irradiated with about 5-10 Gy, about 10-20 Gy, about 20-30 Gy, about 20-40 Gy, about 20-50 Gy, about 10-50 Gy. According to a specific embodiment, the DCs are irradiated with about 10-50 Gy (e.g. 30 Gy).

Any method of producing anti-third party Tcm cells can be used in accordance with the present invention as was previously described in PCT Publication Nos. WO 2010/049935, WO 2012/032526 and WO 2013/035099, incorporated herein by reference.

According to one embodiment, generating an anti-third party cell having a Tcm phenotype may be carried out by a method comprising: (a) contacting peripheral blood mononuclear cells (PBMC) with a third party antigen or antigens in the presence or absence of IL-21 so as to allow enrichment of antigen reactive cells; and (b) culturing the cells resulting from step (a) in the presence of IL-21, IL-15 and IL-7 in an antigen free environment so as to allow proliferation of cells comprising the central memory T-lymphocyte (Tcm) phenotype.

According to one embodiment, the PBMCs in step (a) are contacted with a third party antigen or antigens in the absence of IL-21.

According to one embodiment, the PBMCs in step (a) are contacted with a third party antigen or antigens in the presence of IL-21.

According to one embodiment, the cells resulting from step (a) are cultured in an antigen free environment (e.g. without the addition of an antigen to the cell culture) in the presence of only IL-15. IL-21 and/or IL-7 may optionally be added.

The anti-third party Tcm cells of the present invention are typically generated by first contacting syngeneic (e.g. autologous) or non-syngeneic (e.g. non-autologous such as allogeneic or xenogeneic, as described in further detail below) peripheral blood mononuclear cells (PBMC) with a third party antigen or antigens (such as described above) in a culture supplemented with IL-21 (e.g. in an otherwise cytokine-free culture i.e., without the addition of any additional cytokines). This step is typically carried out for about 12-24 hours, about 12-36 hours, about 12-72 hours, 24-48 hours, 24-36 hours, about 24-72 hours, about 48-72 hours, 1-2 days, 2-3 days, 1-3 days, 2-4 days, 1-5 days, 2-5 days, 2-6 days, 1-7 days, 5-7 days, 2-8 days, 8-10 days or 1-10 days and allows enrichment of antigen reactive cells.

According to a specific embodiment, contacting of syngeneic or non-syngeneic PBMC with a third party antigen or antigens (such as described above) in a culture supplemented with IL-21 (otherwise cytokine-free culture) is effected for 1-5 days (e.g. 3 days).

Contacting syngeneic or non-syngeneic PBMC with a third party antigen or antigens (such as described above) in a culture supplemented with IL-21 is typically carried out in the presence of about 0.001-3000 IU/ml, 0.01-3000 IU/ml, 0.1-3000 IU/ml, 1-3000 IU/ml, 10-3000 IU/ml, 100-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 100-1000 IU/ml, 250-1000 IU/ml, 500-1000 IU/ml, 750-1000 IU/ml, 10-500 IU/ml, 50-500 IU/ml, 100-500 IU/ml, 250-500 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-21.

According to a specific embodiment, the concentration of IL-21 is 50-150 IU/ml (e.g. 100 IU/ml).

According to a specific embodiment, contacting the syngeneic or non-syngeneic PBMC with a third party antigen or antigens is effected in a cytokine-free culture (e.g. supplemented with only IL-21), such a culture condition enables survival and enrichment of only those cells which undergo stimulation and activation by the third party antigen or antigens (i.e. of antigen reactive cells) as these cells secrete cytokines (e.g. IL-2) which enable their survival (all the rest of the cells die under these culture conditions).

The ratio of third party antigen or antigens (e.g. dendritic cell) to PBMC is typically about 1:2 to about 1:10 such as about 1:4, about 1:6, about 1:8 or about 1:10.

According to a specific embodiment, the ratio of third party antigen or antigens (e.g. dendritic cell) to PBMC is about 1:2 to about 1:8 (e.g. 1:5).

Next, the anti-third party cells are cultured in the presence of IL-21, IL-15 and/or IL-7 in an antigen free environment so as to allow proliferation of cells comprising the Tcm phenotype. This step is typically carried out for about 12-24 hours, about 12-36 hours, about 12-72 hours, 24-48 hours, 24-36 hours, about 24-72 hours, about 48-72 hours, 1-20 days, 1-15 days, 1-10 days, 1-5 days, 5-20 days, 5-15 days, 5-10 days, 1-2 days, 2-3 days, 1-3 days, 2-4 days, 2-5 days, 2-8 days, 2-10 days, 4-10 days, 4-8 days, 6-8 days, 8-10 days, 7-9 days, 7-11 days, 7-13 days, 7-15 days, 10-12 days, 10-14 days, 12-14 days, 14-16 days, 14-18 days, 16-18 days or 18-20 days. According to a specific embodiment, the anti-third party cells are cultured in the presence of IL-21, IL-15 and IL-7 in an antigen free environment for about 7-11 days (e.g. 8 days).

This step is typically carried out in the presence of IL-21 at a concentration of about 0.001-3000 IU/ml, 0.01-3000 IU/ml, 0.1-3000 IU/ml, 1-3000 IU/ml, 10-3000 IU/ml, 100-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 100-1000 IU/ml, 250-1000 IU/ml, 500-1000 IU/ml, 750-1000 IU/ml, 10-500 IU/ml, 50-500 IU/ml, 100-500 IU/ml, 250-500 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-21.

According to a specific embodiment, the concentration of IL-21 is 50-150 IU/ml (e.g. 100 IU/ml).

This step is further carried out in the presence of IL-15 at a concentration of about 0.001-3000 IU/ml, 0.01-3000 IU/ml, 0.1-3000 IU/ml, 1-3000 IU/ml, 10-3000 IU/ml, 100-3000 IU/ml, 125-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 100-1000 IU/ml, 125-1000 IU/ml, 250-1000 IU/ml, 500-1000 IU/ml, 750-1000 IU/ml, 10-500 IU/ml, 50-500 IU/ml, 100-500 IU/ml, 125-500 IU/ml, 250-500 IU/ml, 250-500 IU/ml, 125-250 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-15. According to a specific embodiment the concentration of IL-15 is 100-150 IU/ml (e.g. 125 IU/ml).

This step is further carried out in the presence of IL-7 at a concentration of about 0.001-3000 IU/ml, 0.01-3000 IU/ml, 0.1-3000 IU/ml, 1-3000 IU/ml, 10-3000 IU/ml, 30-3000 IU/ml, 100-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 30-1000 IU/ml, 100-1000 IU/ml, 250-1000 IU/ml, 500-1000 IU/ml, 750-1000 IU/ml, 10-500 IU/ml, 30-500 IU/ml, 50-500 IU/ml, 100-500 IU/ml, 250-500 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-7. According to a specific embodiment the concentration of IL-7 is 10-50 IU/ml (30 IU/ml).

The present inventors have collected through laborious experimentation and screening a number of criteria which may be harnessed towards to improving the proliferation of anti-third party cells comprising a central memory T-lymphocyte (Tcm) phenotype being devoid of graft versus host (GVH) reactive cells and/or being enhanced for anti-disease (e.g. GVL) reactive cells.

According to one embodiment, the PBMCs are depleted of adherent cells prior to contacting with a third party antigen or antigens in the presence of IL-21.

According to one embodiment, the PBMCs are depleted of CD4+ and/or CD56+ cells prior to contacting with a third party antigen or antigens in the presence of IL-21.

According to one embodiment, the PBMCs are selected for CD45RA+ cells prior to contacting with a third party antigen or antigens in the presence of IL-21. Depletion of $CD4^+$ and/or CD56+ cells may be carried out using any method known in the art, such as by affinity based purification (e.g. such as by the use of MACS beads, FACS sorter and/or capture ELISA labeling). Such a step may be beneficial in order to increase the purity of the $CD8^+$ cells within the culture (i.e. eliminate other lymphocytes within the cell culture e.g. T $CD4^+$ cells or NK cells) or in order to increase the number of $CD8^+$ T cells.

According to one embodiment, the PBMCs comprise non-adherent cells.

According to one embodiment, the PBMCs comprise CD8+ T cells.

According to one embodiment, the PBMCs comprise naïve CD8+ T cells.

Selection of naïve CD8+ T cells may be effected by selection of cells expressing CD45RA+ and/or cells expressing CD45RO− and may be carried out using any method known in the art, such as by affinity based purification (e.g. such as by the use of MACS beads, FACS sorter and/or capture ELISA labeling).

According to one embodiment, the PBMCs comprise CD45RA+ cells.

An additional step which may be carried out in accordance with the present teachings include culturing the PBMCs cells with a third party antigen or antigens in the presence of IL-21, IL-15 and IL-7 prior to removing the third party antigen or antigens from the cell culture (i.e. prior to generating an antigen free environment).

This step is typically carried out for about 12-24 hours, about 12-36 hours, about 12-72 hours, 24-48 hours, 24-36 hours, about 24-72 hours, about 48-72 hours, 1-2 days, 2-3 days, 1-3 days, 2-4 days, 1-5 days or 2-5 days, and is effected at the same doses of IL-21, IL-15 and IL-7 indicated above. According to a specific embodiment, culturing the PBMCs cells with a third party antigen or antigens in the presence of IL-21, IL-15 and IL-7 is carried out for 12 hours to 4 days (e.g. 1-2 days).

Additionally or alternatively, an additional two step process which allows selection and isolation of activated cells may be carried out. Such a selection step aids in removal of potential host reactive T cells (e.g. alloreactive cells) in situations where the PBMCs are non-syngeneic with respect to the subject (as described in further detail below).

Thus, isolating activated cells may be carried out in a two stage approach. In the first stage activated cells are selected before culturing the cells in the presence of IL-15 and IL-7. This first stage is typically carried out after the initial contacting of the PBMC with a third party antigen or antigens in the presence of IL-21. This selection process picks only those cells which were activated by the third party antigen (e.g. express activation markers as described below) and is typically affected about 12-24 hours, about 24-36 hours, about 12-36 hours, about 36-48 hours, about 12-48 hours, about 48-60 hours, about 12-60 hours, about 60-72 hours, about 12-72 hours, about 72-84 hours, about 12-84 hours, about 84-96 hours, about 12-96 hours, after the initial contacting of the PBMC with a third party antigen or antigens.

According to a specific embodiment, the selection process is effected about 12-24 hours (e.g. 14 hours) after the initial contacting of the PBMC with a third party antigen or antigens.

Isolating activated cells may be effected by affinity based purification (e.g. such as by the use of MACS beads, FACS sorter and/or capture ELISA labeling) and may be effected towards any activation markers including cell surface markers such as, but not limited to, CD69, CD44, CD25, CFSE, CD137 or non-cell surface markers such as, but not limited to, IFN-γ and IL-2. Isolating activated cells may also be effected by morphology based purification (e.g. isolating large cells) using any method known in the art (e.g. by FACS). Typically, the activated cells are also selected for expression of $CD8^+$ cells. Furthermore, any combination of the above methods may be utilized to efficiently isolate activated cells.

According to an embodiment of the present invention, selecting for activated cells is effected by selection of CD137+ and/or CD25+ cells.

The second stage of isolation of activated cells is typically carried out at the end of culturing (i.e. after culturing in an antigen free environment with IL-21, IL-15 and IL-7). This stage depletes alloreactive cells by depletion of those cells which were activated following contacting of the central memory T-lymphocyte (Tcm) with irradiated host antigen presenting cells (APCs e.g. dendritic cells). As mentioned above, isolating activated cells may be effected by affinity based purification (e.g. such as by the use of MACS beads, FACS sorter and/or capture ELISA labeling) and may be effected towards any activation markers including cell surface markers such as, but not limited to, CD69, CD44, CD25, CFSE, CD137 or non-cell surface markers such as, but not limited to, TN-γ and IL-2.

According to an embodiment of the present invention, depleting the alloreactive cells is effected by depletion of CD137+ and/or CD25+ cells and/or IFNγ-capture.

Following are exemplary protocols which can be used according to some embodiments of the invention.

According to one embodiment of the invention, there is provided a method of generating an isolated cell having a central memory phenotype, the cell being a tolerance-inducing cell and capable of homing to the lymph nodes following transplantation, the method comprising: (a) contacting peripheral blood mononuclear cells (PBMC) with a third party antigen or antigens in the presence of IL-21 (e.g. for 12 hours to 5 days) so as to allow enrichment of antigen reactive cells; and (b) culturing the cells resulting from step (a) in the presence of IL-21, IL-15 and IL-7 in an antigen free environment (e.g. for 5-20 days) so as to allow proliferation of anti-third party cells comprising the central memory T-lymphocyte (Tcm) phenotype.

According to one embodiment, the method further comprises (c) separating the cells resulting from step (b) into single cell suspensions.

According to one embodiment, the method further comprises depleting adherent cells from the PBMC prior to step (a).

According to one embodiment, the method further comprises depleting CD4+ and/or CD56+ cells from the PBMC prior to step (a).

According to one embodiment, the method further comprises selecting for activated cells following step (a) and prior to step (b).

According to one embodiment, the method further comprises selecting for activated cells is effected by selection of CD137+ and/or CD25+ cells.

According to one embodiment of the invention, there is provided a method of generating an isolated cell having a central memory phenotype, the cell being a tolerance-inducing cell and capable of homing to the lymph nodes following transplantation, the method comprising: (a) treating non-adherent peripheral blood mononuclear cells (PBMC) with an agent capable of depleting CD4+ and/or CD56+ cells so as to obtain CD8+ T cells; (b) contacting the CD8+ T cells with third party dendritic cells in the presence of IL-21 (e.g. for 12 hours to 5 days) so as to allow enrichment of antigen reactive cells; (c) culturing the cells resulting from step (b) with the third party dendritic cells in the presence of IL-21, IL-15 and IL-7 (e.g. for 12 hours to 3 days); and (d) culturing the cells resulting from step (c) in the presence of IL-21, IL-15 and IL-7 in an antigen free environment (e.g. for 5-20 days) so as to allow proliferation of cells comprising the central memory T-lymphocyte (Tcm) phenotype.

According to one embodiment, the method further comprises separating the cells resulting from step (d) into single cell suspensions.

According to one embodiment, the anti-third party cells comprising the Tcm phenotype comprise a $CD3^+$, $CD8^+$, $CD62L^+$, $CD45RA^-$, $CD45RO^+$ signature.

It will be appreciated that at least 30%, at least 40%, at least 50%, at least 55%, at least 60%, at least 65%, at least 70%, at least 75%, at least 80%, at least 85%, at least 90%, at least 95% or even 100% of the anti-third party cells are CD3+CD8+ cells. According to a specific embodiment, the anti-third party cells comprise about 70-90% CD3+CD8+ cells.

It will be appreciated that at least 30%, at least 40%, at least 50%, at least 55%, at least 60%, at least 65%, at least 70%, at least 75%, at least 80%, at least 85%, at least 90%, at least 95% or even 100% of the CD3+CD8+ cells have the Tcm cell signature. According to a specific embodiment, about 30-80% of the CD3+CD8+ cells have the Tcm cell signature (e.g. 40-50%).

According to one embodiment, at least 50% of the cells are CD3+CD8+ cells of which at least 50% have the signature.

Thus, the cells of the invention having a central memory T-lymphocyte (Tcm) phenotype are not naturally occurring and are not a product of nature. These cells are typically produced by ex-vivo manipulation (i.e. exposure to a third party antigen or antigens in the presence of specific cytokines).

As mentioned, the Tcm cell of the invention is transduced with a polynucleotide encoding a cell surface receptor comprising a T cell receptor signaling module.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a cell, or from a tissue, e.g., from a human body.

The isolated polynucleotide can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The polynucleotide according to some embodiments of the invention may comprise a single polynucleotide comprising a nucleic acid sequence encoding the extracellular domain, the transmembrane domain and/or the signaling module of the cell surface receptor (e.g. tg-TCR and/or CAR). Alternatively, two or more polynucleotides may be used wherein one polynucleotide may comprise a nucleic acid sequence which encodes, for example, the extracellular domain and transmembrane domain and another polynucleotide may comprise a nucleic acid sequence which encodes the signaling module.

According to an aspect of some embodiments of the invention there is provided a nucleic acid construct comprising an isolated polynucleotide comprising a nucleic acid sequence encoding the molecule of some embodiments of the invention and a cis-acting regulatory element for directing transcription of the isolated polynucleotide in a host cell.

Thus, the expression of natural or synthetic nucleic acids encoding the cell surface receptor (e.g. tg-TCR or CAR molecule) of the invention is typically achieved by operably linking a nucleic acid encoding the cell surface receptor (e.g. tg-TCR or CAR) polypeptide or portions thereof to a cis-acting regulatory element (e.g., a promoter sequence), and incorporating the construct into an expression vector.

The nucleic acid construct of the invention may also include an enhancer, a transcription and translation initiation sequence, transcription and translation terminator and a polyadenylation signal, a 5' LTR, a tRNA binding site, a packaging signal, an origin of second-strand DNA synthesis, and a 3' LTR or a portion thereof; additional polynucleotide sequences that allow, for example, the translation of several proteins from a single mRNA such as an internal ribosome entry site (IRES) and sequences for genomic integration of the promoter-chimeric polypeptide; sequences engineered to enhance stability, production, purification, yield or toxicity of the expressed peptide.

Enhancers regulate the frequency of transcriptional initiation. Typically, promoter elements are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1.alpha. (EF-1.alpha.). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

The isolated polynucleotide of the invention can be cloned into a number of types of vectors. For example, the isolated polynucleotide can be cloned into a vector including, but not limited to a plasmid, a phagemid, a phage derivative, an animal virus, and a cosmid. Vectors of particular interest include expression vectors, replication vectors, probe generation vectors, and sequencing vectors.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Currently preferred in vivo or in vitro nucleic acid transfer techniques include transfection with viral or non-viral constructs, such as adenovirus, lentivirus, Herpes simplex I virus, or adeno-associated virus (AAV). Recombinant viral vectors offer advantages such as lateral infection and targeting specificity. Introduction of nucleic acids by viral infection offers several advantages over other methods such as lipofection and electroporation, since higher transfection efficiency can be obtained due to the infectious nature of viruses.

Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

According to some embodiments of the invention, the nucleic acid construct of the invention is a viral vector.

Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes.

Furthermore, lentiviral vectors offer a larger gene insertion capacity and also have the added advantage of low immunogenicity. Alternatively, gamma-retroviral vectors may be used. Gamma-retroviral vectors have good transduction efficiency and no vector-associated toxicity [see e.g. Zhang and Morgan, Adv Drug Deliv Rev. (2012) supra].

For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

In order to assess the expression of a cell surface receptor (e.g. tg-TCR or CAR) polypeptide or portions thereof, the nucleic acid construct to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tel et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Various methods can be used to introduce the nucleic acid construct of the invention into a host cell, e.g., mammalian, bacterial, yeast, or insect cell. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, physical, chemical, or biological means (e.g., stable or transient transfection, lipofection, electroporation and infection with recombinant viral vectors). In addition, see U.S. Pat. Nos. 5,464,764 and 5,487,992 for positive-negative selection methods.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Biological methods for introducing a polynucleotide of interest into a host cell include the use of DNA and RNA vectors (as described above). Viral vectors, and especially retroviral vectors, have become the most widely used method for inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

In the case where a non-viral delivery system is utilized, an exemplary delivery vehicle is a liposome.

"Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution.

The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as non-uniform aggregates of lipid molecules. Also contemplated are lipofectamine-nucleic acid complexes.

The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG"); and other lipids may be obtained from Avanti Polar Lipids, Inc, (Birmingham, Ala.). Additionally or alternatively, the DOTMA, DOPE, and DC-Chol [Tonkinson et al., Cancer Investigation, 14(1): 54-65 (1996)] lipids can be used. Stock solutions of lipids in chloroform or chloroform/methanol can be stored at about −20.degree. C. Chloroform is used as the only solvent since it is more readily evaporated than methanol.

Another exemplary non-viral delivery system which may be used in accordance with the present invention is a transposon-based non-viral gene delivery system, such as e.g. Sleeping Beauty or PiggyBac.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

It will be appreciated that the cell transduced with the cell surface receptor (e.g. tg-TCR and/or CAR) may further be genetically modified to repress expression of at least one endogenous immunological checkpoint gene in the cell.

The immunological checkpoint gene may comprise a PD or CTLA gene.

As used herein the term "immunological checkpoint gene" refers to any gene that is involved in an inhibitory process (e.g., feedback loop) that acts to regulate the amplitude of an immune response, for example an immune inhibitory feedback loop that mitigates uncontrolled propagation of harmful immune responses.

Non-limiting examples of immunological checkpoint genes include members of the extended CD28 family of receptors and their ligands as well as genes involved in co-inhibitory pathways (e.g., CTLA-4 and PD-1).

Thus, according to one embodiment PD1 and/or CTLA-4-targeted nucleases or transcription repressors can be utilized as discussed in U.S. Patent Application No. 20140120622, incorporated herein by reference.

Additionally or alternatively, immune checkpoint proteins, which regulate activation or function of a T cell, including for example, PD1, PDL-1, B7H2, B7H4, CTLA-4, CD80, CD86, LAG-3, TIM-3, KIR, IDO, CD19, OX40, 4-1BB (CD137), CD27, CD70, CD40, GITR, CD28 and/or ICOS (CD278), may be modulated (e.g. upregulated or downregulated as needed) in the transduced cell by the use of an immune checkpoint regulator.

According to specific embodiments, the immune-checkpoint regulator is selected from the group consisting of anti-CTLA4, anti-PD-1, anti-PDL-1, CD40 agonist, 4-1BB agonist, GITR agonist and OX40 agonist.

According to an aspect of some embodiments of the invention there is provided a population of cells comprising the isolated cell of some embodiments of the invention.

The isolated cell or population of cells of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the cells of some embodiments of the invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences", Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method. Alternately, one may administer the pharmaceutical composition in a local rather than systemic manner, for example, via injection of the pharmaceutical composition directly into a tissue region of a patient.

According to one embodiment, the route of administration includes, for example, an injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the pharmaceutical composition of the present invention is administered to a patient by intradermal or subcutaneous injection. In another embodiment, the pharmaceutical composition of the present invention is preferably administered by i.v. injection. The pharmaceutical composition may be injected directly into a tumor, lymph node, or site of infection.

Pharmaceutical compositions of some embodiments of the invention may be manufactured by processes well known in the art, e.g., by means of conventional mixing, dissolving, granulating, dragee-making, levitating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion.

Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes.

Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of the invention include compositions wherein the active ingredients are contained in an amount effective to achieve the intended purpose. More specifically, a therapeutically effective amount means an amount of active ingredients effective to prevent, alleviate or ameliorate symptoms of a pathology or prolong the survival of the subject being treated.

Determination of a therapeutically effective amount is well within the capability of those skilled in the art, especially in light of the detailed disclosure provided herein.

When "therapeutic amount" is indicated, the precise amount of the compositions of the present invention to be administered can be determined by a physician with consideration of individual differences in age, weight, disease state, e.g. tumor size, extent of infection or metastasis, and the condition of the patient (subject). It can generally be stated that a pharmaceutical composition comprising the cells described herein may be administered at a dosage of $10^4$ to $10^9$ cells/kg body weight, including all integer values within those ranges.

For example, the number of cells infused to a recipient should be more than $1\times10^4$/Kg body weight. The number of cells infused to a recipient should typically be in the range of $1\times10^3$/Kg body weight to $1\times10^4$/Kg body weight, range of $1\times10^4$/Kg body weight to $1\times10^5$/Kg body weight, range of $1\times10^4$/Kg body weight to $1\times10^6$/Kg body weight, range of $1\times10^4$/Kg body weight to $10\times10^7$/Kg body weight, range of $1\times10^4$/Kg body weight to $1\times10^8$/Kg body weight, range of $1\times10^5$/Kg body weight to $1\times10^5$/Kg body weight, range of $1\times10^4$/Kg body weight to $1\times10^6$/Kg body weight, range of $1\times10^6$/Kg body weight to $10\times10^7$/Kg body weight, range of $1\times10^5$/Kg body weight to $10\times10^7$/Kg body weight, range of $1\times10^6$/Kg body weight to $1\times10^8$/Kg body weight, or range of $1\times10^6$/Kg body weight to $1\times10^9$/Kg body weight. According to a specific embodiment, the number of cells infused to a recipient should be in the range of $1\times10^6$/Kg body weight to $10\times10^8$/Kg body weight.

The cell compositions of some embodiments of the invention may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

For example, the effect of the active ingredients (e.g., the cells of some embodiments of the invention) on the pathology can be evaluated by monitoring the level of markers, e.g., hormones, glucose, peptides, carbohydrates, etc. in a biological sample of the treated subject using well known methods (e.g. ELISA, FACS, etc) or by monitoring the tumor size using well known methods (e.g. ultrasound, CT, MRI, etc).

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

According to some embodiments of the invention, the therapeutic agent of the invention can be provided to the subject in conjunction with other drug(s) designed for treating the pathology [combination therapy, (e.g., before, simultaneously or following)].

In certain embodiments of the present invention, the cells of some embodiments of the invention are administered to a patient in conjunction with any number of relevant treatment modalities, including but not limited to treatment with agents such as antiviral agents (e.g. Ganciclovir, Valaciclovir, Acyclovir, Valganciclovir, Foscarnet, Cidofovir, Maribavir, Leflunomide); chemotherapeutic agents (e.g. antineoplastic agents, such as but not limited to, Alkylating agents including e.g. Cyclophosphamide, Busulfan, Mechlorethamine or mustine (HN2), Uramustine or uracil mustard, Melphalan, Chlorambucil, Ifosfamide, Bendamustine, Nitrosoureas Carmustine, Lomustine, Streptozocin, Thiotepa, Cisplatin, Carboplatin, Nedaplatin, Oxaliplatin, Satraplatin, Triplatin tetranitrate, Procarbazine, Altretamine, Triazenes (dacarbazine, mitozolomide, temozolomide), Dacarbazine, Temozolomide, Myleran, Busulfex, Fludarabine, Dimethyl mileran or Cytarabine); agents for the treatment of MS (e.g. natalizumab); or agents for the treatment of psoriasis (e.g. efalizumab).

In further embodiments, the cells of some embodiments of the invention may be used in combination with chemotherapy, radiation, immunosuppressive agents (e.g. cyclosporin, azathioprine, methotrexate, mycophenolate, and FK506), antibodies, or other immunoablative agents (discussed in further detail below).

In a further embodiment, the cell compositions of some embodiments of the invention are administered to a patient in conjunction with (e.g., before, simultaneously or following) bone marrow transplantation.

In a further embodiment, the cell compositions of some embodiments of the invention are administered to a patient following a T cell ablative therapy using, for example, chemotherapy agents such as, fludarabine, external-beam radiation therapy (XRT), cyclophosphamide, or antibodies such as OKT3 or CAMPATH.

In another embodiment, the cell compositions of the present invention are administered following B-cell ablative therapy such as agents that react with CD20, e.g., Rituxan.

The combination therapy may increase the therapeutic effect of the agent of the invention in the treated subject.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The kit may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to one embodiment, the kit further comprises a chemotherapeutic agent (e.g. antineoplastic agent, as discussed in detail hereinabove).

According to one embodiment, the kit further comprises an antiviral agent (as discussed in detail hereinabove).

According to an aspect of some embodiments of the invention, there is provided a method of treating a disease in a subject in need thereof, the method comprising administering to the subject a therapeutically effective amount of the population of cells of some embodiments of the invention, thereby treating the subject.

According to an aspect of some embodiments of the invention, there is provided a therapeutically effective amount of the population of cells of some embodiments of the invention for use in treating a disease in a subject in need thereof.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, preferably human beings at any age or gender which suffer from the pathology.

The pathology can be, but is not limited to, a malignant disease (cancer), an infectious disease (e.g. viral infection, bacterial infection, fungal infection, protozoan infection or parasitic infections), an allergy and/or an autoimmune disease.

Cancerous Diseases

Malignant diseases (also termed cancers) which can be treated by the method of some embodiments of the invention can be any solid or non-solid tumor and/or tumor metastasis.

Examples of cancer include, but are not limited to, carcinoma, lymphoma, blastoma, sarcoma, and leukemia. More particular examples of such cancers include squamous cell cancer, soft-tissue sarcoma, Kaposi's sarcoma, melanoma, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, rectal cancer, endometrial or uterine carcinoma, carcinoid carcinoma, salivary gland carcinoma, kidney or renal cancer, liver cancer, prostate cancer, vulval cancer, thyroid cancer, hepatic carcinoma, mesothelioma, multiple myeloma, post-transplant lymphoproliferative disorder (PTLD), and various types of head and neck cancer (e.g. brain tumor). The cancerous conditions amenable for treatment of the invention include metastatic cancers.

According to one embodiment, the malignant disease is a hematological malignancy. Exemplary hematological malignancies include, but are not limited to, leukemia [e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia, T-cell acute lymphocytic leukemia (T-ALL) and B-cell chronic lymphocytic leukemia (B-CLL)] and lymphoma [e.g., Hodgkin's disease, non-Hodgkin's lymphoma, Burkitt, cutaneous T cell, histiocytic, lymphoblastic, T cell, thymic, B cell, including low grade/follicular; small lymphocytic (SL) NHL; intermediate grade/follicular NHL; intermediate grade diffuse NHL; high grade immunoblastic NHL; high grade lymphoblastic NHL; high-grade small non-cleaved cell NHL; bulky disease NHL; mantle cell lymphoma; AIDS-related lymphoma; and Waldenstrom's Macroglobulinemia].

According to a specific embodiment, the malignant disease is a leukemia, a lymphoma, a myeloma, a melanoma, a sarcoma, a neuroblastoma, a colon cancer, a colorectal cancer, a breast cancer, an ovarian cancer, an esophageal cancer, a synovial cell cancer or a pancreatic cancer.

According to some embodiments of the invention, the pathology is a solid tumor.

According to some embodiments of the invention, the pathology is a tumor metastasis.

According to some embodiments of the invention, the pathology is a hematological malignancy.

According to some embodiments of the invention, the pathology is a leukemia or a lymphoma.

Exemplary malignant diseases which are treatable by the methods of some embodiments of the invention are listed in Tables 1 and 2, below.

TABLE 1

Clinical applications utilizing tg-TCR transduced cells with optional preconditioning regimens

| Target Ag of tg-TCR | Disease | Preconditioning |
|---|---|---|
| MART-1 | melanoma | Cy + Flud (cyclophosphamide + fludarabine) |
| MART-1 | melanoma | Cy + Flud |
| gp100 | melanoma | Cy + Flud |
| p53/gp100 | breast cancer melanoma esophageal cancer | Cy + Flud |
| CEA | colorectal cancer | Cy + Flud |
| NY-ESO-1 | melanoma synovial cell cancer | Cy + Flud |
| MAGE-A3 | melanoma synovial cell cancer esophageal cancer | Cy + Flud |
| MAGE-A3 | melanoma myeloma | Cy Melphalan and auto stem cell transplantation (SCT) |

(adapted from Fujiwara, Pharmaceuticals (2014), 7: 1049-1068)

TABLE 2

Clinical applications utilizing CAR transduced cells with optional preconditioning regimens

| Target Ag of CAR | Disease | Preconditioning |
|---|---|---|
| L1-cell adhesion molecule | neuroblastoma | none |
| HER2 | colon cancer with lung/liver metastasis | Cy + Flud |
| GD2 | neuroblastoma | none |
| CD19 | Chronic lymphocytic leukemia (CLL) | CTx for CLL |
| CD19 | CLL | none |
| | Acute lymphocytic leukemia (ALL) | Cy (1500 mg or 3000 mg) |
| CD19 | CLL follicular cell lymphoma (FL) | Cy + Flud |
| CD19 | B-cell acute lymphoblastic leukemia (B-ALL) | Cy (1500 mg or 3000 mg) |
| CD19 | ALL | CTx for ALL |
| CD19 | refractory B-ALL ph+ | Cy (1500 mg or 3000 mg) |
| CD20 | Mantle cell lymphoma (MCL) FL | Cy (1000 mg/m2) |

(adapted from Fujiwara, Pharmaceuticals (2014), 7: 1049-1068)

According to a specific embodiment, the malignant disease is a leukemia, a lymphoma, a myeloma, a melanoma, a sarcoma, a neuroblastoma, a colon cancer, a colorectal cancer, a breast cancer, an ovarian cancer, an esophageal cancer, a synovial cell cancer and a pancreatic cancer.

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection and rabies.

According to a specific embodiment, the viral disease is selected from the group consisting of an immunodeficiency virus (HIV), an influenza, a Cytomegalovirus (CMV), a T-cell leukemia virus type 1 (TAX), a hepatitis C virus (HCV) and a hepatitis B virus (HBV).

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis [Krenn V. et al., Histol Histopathol (2000) 15 (3):791; Tisch R and McDevitt H O. Proc Natl Acad Sci USA (1994) 18; 91(2): 437-438] and ankylosing spondylitis [Jan Voswinkel et al., Arthritis Res (2001) 3 (3): 189].

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydenham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

According to a specific embodiment, the autoimmune disease is selected from the group consisting of a type 1 diabetes, a multiple sclerosis, a rheumatoid arthritis, a celiac and a stroke.

As mentioned, the cells of the invention can be obtained from any cell donor. Thus, the subject to be treated can be a human subject while the cells can be obtained from a syngeneic (e.g. autologous) or non-syngeneic donor (e.g. allogeneic or xenogeneic with respect to the recipient).

As used herein, the term "syngeneic" cells refer to cells which are essentially genetically identical with the subject or essentially all lymphocytes of the subject. Examples of syngeneic cells include cells derived from the subject (also referred to in the art as "autologous"), from a clone of the subject, or from an identical twin of the subject.

As used herein, the term "non-syngeneic" cells refer to cells which are not essentially genetically identical with the subject or essentially all lymphocytes of the subject, such as allogeneic cells or xenogeneic cells.

As used herein, the term "allogeneic" refers to cells which are derived from a donor who is of the same species as the subject, but which is substantially non-clonal with the subject. Typically, outbred, non-zygotic twin mammals of the same species are allogeneic with each other. It will be appreciated that an allogeneic cell may be HLA identical, partially HLA identical or HLA non-identical (i.e. displaying one or more disparate HLA determinant) with respect to the subject.

As used herein, the term "xenogeneic" refers to a cell which substantially expresses antigens of a different species relative to the species of a substantial proportion of the lymphocytes of the subject. Typically, outbred mammals of different species are xenogeneic with each other.

The present invention envisages that xenogeneic cells are derived from a variety of species. Thus, according to one embodiment, the cells may be derived from any mammal. Suitable species origins for the cells comprise the major domesticated or livestock animals and primates. Such animals include, but are not limited to, porcines (e.g. pig), bovines (e.g., cow), equines (e.g., horse), ovines (e.g., goat, sheep), felines (e.g., *Felis domestica*), canines (e.g., *Canis domestica*), rodents (e.g., mouse, rat, rabbit, guinea pig, gerbil, hamster), and primates (e.g., chimpanzee, rhesus monkey, macaque monkey, marmoset).

Cells of xenogeneic origin (e.g. porcine origin) are preferably obtained from a source which is known to be free of zoonoses, such as porcine endogenous retroviruses. Similarly, human-derived cells or tissues are preferably obtained from substantially pathogen-free sources.

According to one embodiment, the cells are non-syngeneic with the subject.

According to one embodiment, the cells are allogeneic with the subject.

According to one embodiment, the cells are syngeneic with the subject (e.g. autologous).

According to an embodiment of the present invention, the subject is a human being and the cells are from a human origin (e.g. non-autologous).

According to one embodiment, the subject is a human being and the cells are from a xenogeneic origin (e.g. porcine origin).

Any method known in the art may be employed to obtain cells for transplantation. Thus, for example, immune cells (e.g. T cells, B cells, NK cells, DCs) may be obtained by collecting peripheral blood from a donor. Methods of collecting peripheral blood are well known in the art and include, but are not limited to, drawing of up to 500-1000 ml whole blood from a donor and collection in a container containing an anti-coagulant (e.g. heparin or citrate) or by apheresis, a procedure in which the peripheral blood of an individual is passed through an apparatus, yielding a predominant constituent (e.g. mononuclear cells such as lymphocytes, monocytes or dendritic cells), and returning the other constituents to the subject's circulation. Alternatively, cells may be obtained by in-vitro or ex-vivo culture of cells. It will be appreciated that the cells of the invention may be of fresh or frozen (e.g., cryo-preserved) preparations.

Depending on the transplantation context, in order to facilitate engraftment of the cells, the method may further advantageously comprise conditioning the subject under sublethal, lethal or supralethal conditions prior to the transplanting.

As used herein, the terms "sublethal", "lethal", and "supralethal", when relating to conditioning of subjects of the present invention, refer to myelotoxic and/or lymphocytotoxic treatments which, when applied to a representative population of the subjects, respectively, are typically: non-lethal to essentially all members of the population; lethal to some but not all members of the population; or lethal to essentially all members of the population under normal conditions of sterility.

According to some embodiments of the invention, the sublethal, lethal or supralethal conditioning comprises total body irradiation (TBI), total lymphoid irradiation (TLI, i.e. exposure of all lymph nodes, the thymus, and spleen), partial body irradiation (e.g. specific exposure of the colon, breast, etc.), myeloablative conditioning and/or non-myeloablative conditioning, e.g. with different combinations including, but not limited to, co-stimulatory blockade, chemotherapeutic agent and/or antibody immunotherapy. According to some embodiments of the invention, the conditioning comprises a combination of any of the above described conditioning protocols (e.g. chemotherapeutic agent and TBI, co-stimulatory blockade and chemotherapeutic agent, antibody immunotherapy and chemotherapeutic agent, etc.).

According to one embodiment, the TBI comprises a single or fractionated irradiation dose within the range of 0.5-1 Gy, 0.5-1.5 Gy, 0.5-2.5 Gy, 0.5-5 Gy, 0.5-7.5 Gy, 0.5-10 Gy, 0.5-15 Gy, 1-1.5 Gy, 1-2 Gy, 1-2.5 Gy, 1-3 Gy, 1-3.5 Gy, 1-4 Gy, 1-4.5 Gy, 1-1.5 Gy, 1-7.5 Gy, 1-10 Gy, 2-3 Gy, 2-4 Gy, 2-5 Gy, 2-6 Gy, 2-7 Gy, 2-8 Gy, 2-9 Gy, 2-10 Gy, 3-4 Gy, 3-5 Gy, 3-6 Gy, 3-7 Gy, 3-8 Gy, 3-9 Gy, 3-10 Gy, 4-5 Gy, 4-6 Gy, 4-7 Gy, 4-8 Gy, 4-9 Gy, 4-10 Gy, 5-6 Gy, 5-7 Gy, 5-8 Gy, 5-9 Gy, 5-10 Gy, 6-7 Gy, 6-8 Gy, 6-9 Gy, 6-10 Gy, 7-8 Gy, 7-9 Gy, 7-10 Gy, 8-9 Gy, 8-10 Gy, 10-12 Gy or 10-15 Gy.

According to a specific embodiment, the TBI comprises a single or fractionated irradiation dose within the range of 1-7.5 Gy.

According to one embodiment, the conditioning step is effected by conditioning the subject under supralethal conditions, such as under myeloablative conditions.

Alternatively, the conditioning step may be effected by conditioning the subject under lethal or sublethal conditions, such as by conditioning the subject under myeloreductive conditions or non-myeloablative conditions.

According to one embodiment, the conditioning step is effected by conditioning the subject with a myeloablative drug (e.g. Busulfan or Melphalan) or a non-myeloablative drug (e.g. Cyclophosphamide and or Fludarabine).

Examples of conditioning agents which may be used to condition the subject include, without limitation, irradiation, pharmacological agents, and tolerance-inducing cells (as described herein).

Examples of pharmacological agents include myelotoxic drugs, lymphocytotoxic drugs and immunosuppressant drugs (discussed in detail below).

Examples of myelotoxic drugs include, without limitation, busulfan, dimethyl mileran, melphalan and thiotepa.

Additionally or alternatively, the method may further comprise conditioning the subject with an immunosuppressive regimen prior to, concomitantly with, or following transplantation of the cells.

Examples of suitable types of immunosuppressive regimens include administration of immunosuppressive drugs and/or immunosuppressive irradiation.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Examples of immunosuppressive agents include, but are not limited to, Tacrolimus (also referred to as FK-506 or fujimycin, trade names: Prograf, Advagraf, Protopic), Mycophenolate Mofetil, Mycophenolate Sodium, Prednisone, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, tramadol, rapamycin (sirolimus) and rapamycin analogs (such as CCI-779, RAD001, AP23573). These agents may be administered individually or in combination.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Animals

Female 6 to 12 week old BALB/c, CB6 (F1) and C57BL/6 mice were obtained from Harlan Laboratories or grown at the animal facility at Weizmann Institute of Science. All mice were kept in small cages (5 animals in each cage) and fed sterile food and acid water. All studies were approved by the Weizmann Institute of Science Institutional Animal Care and Use Committee.

Preparation of Host Nonreactive Mouse Anti-3$^{rd}$-Party Tcm

Anti-third-party Tcm were prepared as previously described [Ophir E et al., Blood (2010) 115: 2095-2104] briefly, splenocytes of the donor mice were cultured against irradiated third-party splenocytes for 60 hours under cytokine deprivation. Subsequently, CD8$^+$ cells were positively selected using Magnetic Particles (BD Pharmingen) and cultured in an Ag-free environment. rhIL-15 (20 ng/mL; R&D Systems) was added every second day. To attain a purified population at the end of the culture (day 16), the Tcm cells were positively selected for CD62L expression by magnetic-activated cell sorting [MACS, Miltenyi, Bergisch Gladbach, Germany].

Bone Marrow Transplant

1. Long bones were harvested from Balb/c or C57BL/6 mice [either Nude or wild type (WT)]. Bone marrow was extracted by flushing or grinding the bones to reach a single cell suspension. Some preparations harvested from WT mice were subjected to T-cell depletion by magnetic-activated cell sorting. Bone marrow was counted and brought to the correct concentration and was then injected to mice i.v. to the tail vein or intra-orbitally.

2. Prior to transplantation, the mice were subjected to a conditioning regimen. Reduced intensity conditioning (RIC) comprised either subjecting the mice to sub-lethal irradiation doses (i.e. irradiation dose which recipient mice could recover from spontaneously) or subjecting the mice to low dosage of myeloablative (e.g. Busulphan) or non-myeloablative (e.g. Cyclophosphamide) drugs. Total body irradiation (TBI) was administered using either gamma-ray machine or x-ray (e.g. XRAD-320). Drugs were administered by i.v., s.c., i.p. or orally.

OT1+ Cell Transplantation

Lymph nodes and/or spleens were harvested from OT-1 transgenic mice. Mice were either OT-1 mice carrying CD45.1 gene and/or on the background of a RAG−/− mutation. Alternatively, OT-1 mice were F1-OT1 mice, progeny of hostXOT-1 mice, useful for elimination of allogeneic phenomena. Single cell suspensions were created and were then subjected to T-cell purification by magnetic-activated cell sorting [MACS, Miltenyi, Bergisch Gladbach, Germany]. Purity of the resulting OT-1 T-cell population was tested via FACS. Cells were then injected as 'fresh' cells or otherwise were cultured ex-vivo to produce Tcm cells as described above, i.e. by third party activation towards irradiated splenocytes from an ovalbumin expressing mouse. OT-1 Tcm cells were then injected as described herein.

Flow Cytometric Analysis

Fluorescence-activated cell sorting (FACS) analysis was performed using a modified Becton Dickinson FACScan. Cells were stained with labeled antibodies specific for Vα2, Vβ5, H2Dd, H2Kb, CD45.1, CD45.2, CD8a, CD4, CD25, CD69, CD19 (Biolegend; BD; Miltenyi).

CTL Activity Assay ($^{51}$Cr Assay)

Mice were sacrificed, spleens and LNs were harvested and cells were selected for CD8$^+$ (and negatively selected for H-2D$^d$ to exclude 'Tcm'). These naive HTC were tested for their killing ability of either C3H (H-2$^k$) or BALB/c (H-2$^d$) targets in a chromium release assay. BALB/c and C3H splenocytes, used as target cells, were pretreated with 2 μg/ml concanavalinA (Sigma, St. Louis, Mo.) for 48 hours and exposed to 70 μCi $^{51}$Cr (Perkin Elmer, Wellesley, Mass.) for 1 hour. Effector cells were prepared from CD8+ selected cells from C57BL/6 mice and were incubated for 6 days in different dilutions against BALB/c or C3H splenocytes in 12 replicates for each dilution in a 96-well plate with IL-2 (20 U/ml). At day 6, titrated numbers of effector cells and $5 \times 10^3$ $^{51}$Cr-labeled targets were mixed in V-shape bottomed plates at various effector/target (E:T) ratios. Cytotoxic activity was measured in a 4 hour $^{51}$Cr release assay. Percentage of specific lysis was calculated as (experimental release−spontaneous release)/(maximal release−spontaneous release)×100. The release of $^{51}$Cr by target cells cultured in medium alone, or lysed with 1% SDS, was defined as spontaneous release or total release, respectively.

Peripheral Blood Mononuclear Cells (PBMC)

PBMC were isolated from whole blood of patients and from healthy volunteers by Ficoll density gradient centrifugation. When indicated the cells were typed for Class I HLA by serological methods as previously described [Manual of Tissue Typing Techniques. Washington D.C., National Institute of Allergy and Infectious Diseases, NIH DHEW Publication 76-545, 1976, p 22].

Dendritic Cell Generation

Monocytes were isolated by plastic adherence and cultured in 6-well plates using 3 ml of Cellgro DC medium supplemented with 1% human serum and penicillin/streptomycin plus GM-CSF (800 IU/ml) and IL-4 (20 ng/ml) (Peprotech, Hamburg, Germany). After 48 h of culture, 1.5 ml of medium was added (+GM-CSF at 1600 IU/ml and IL4 at 20 ng/ml). 24 h later, non-adherent cells were harvested, and large cells (mostly immature DC) were counted, resuspended in fresh medium containing GM-CSF 800 IU/ml, IL-4 20 ng/ml, LPS from *E. coli* 055:B5 at 10 ng/ml (Sigma, Deisenhofen, Germany) and IFNγ (Peprotech, 100 IU/ml), and plated at approximately 106 DC per well in 2 ml and incubated overnight. The next day, non-adherent cells were discarded, and adherent DC were gently removed using cold PBS/1% HS after incubation on ice for 20 minutes. Large cells consisting of mature DC were counted. The cells were irradiated with 30 Gy to avoid outgrowth of few potentially contaminating NK- or memory T-cells and were then used for T-cell stimulation.

Isolation of Naïve CD8 T-Cells from PBMC

Naïve CD8 T cells were isolated by initial negative selection using a CD8 negative selection kit (Miltenyi, Bergisch Gladbach, Germany) according to the manufacturer's instructions. Antigen-experienced CD8+ T-cells were then depleted using CD45RO-beads and on LD column.

Generation of Anti-3rd Party Central Memory Human CD8 T-Cells

Naïve CD8 T cells were isolated and resuspended in T-cell medium supplemented with IL-21 (Peprotech, 30 ng/ml). Irradiated DCs were added at a 1:4 DC:T-cell ratio with $4 \times 10^5$ T-cells per well of a 48-well plate. Total volume of each well was 500 µl.

72 h after initiation of the culture, 500 µl T-cell medium with IL-7 and IL-15 (Peprotech, 5 ng/ml final concentrations) were added and cells were subsequently fed every 2-3 days as outline in the results section.

Statistical Analysis

The analysis of survival data was performed using Kaplan-Meier curves (log-rank test). Comparison of means was conducted using the Student t test.

Example 1

MHC Mismatched Tcm Survive in Host Mice Under Syngeneic Bone Marrow Settings and Exert Specific Veto Activity Considering that syngeneic bone marrow transplant (BMT), even when administered in the context of lethal total body irradiation (TBI) is by far safer in humans compared to allogeneic BMT, the present inventors first sought out to determine whether adoptively transferred F1-Tcm cells survive the attack of host anti-donor HTC when infused in conjunction with syngeneic TDBMT (FIGS. 1A-B). As can be seen in FIGS. 2A-B, F1-Tcm persisted in the peripheral blood at day 60 post-transplantation. Tcm cells comprised some 13%±10 of the total CD8+ compartment (data not shown). Next, to evaluate the ability of Tcm to induce deletion of antigen-specific clones within the wild type polyclonal HTC population and to verify that remaining HTCs retain their functionality, a chromium release killing assay was employed. Results show that $H2^bCD8^+$ HTC from Tcm treated mice displayed significantly reduced killing of $H-2^d$ targets and retained killing capacity of $H-2^k$ targets, while mice not treated with Tcm (i.e. BM alone group) displayed similar levels of killing for both cell types (FIG. 3). These results indicate that Tcm exert specific-veto activity upon a polyclonal-HTC population and confirm that the clones not deleted by the Tcm, retain their functionality. Subsequently, these experiments were repeated in mice conditioned with reduced intensity conditioning (RIC), more suitable for clinical implementation. Hence, studies in 5.5 Gy TBI sublethally irradiated Balb/c mice, injected with syngeneic T cell depleted bone marrow (TDBMT) and allogeneic (Balb×Black) F1 Tcm (illustrated in FIG. 1C), yielded similar results (FIG. 4). Tcm cells were present in peripheral blood of these mice for more than 15 months (when experiment was terminated, data not shown). Thus, the survival of MHC mismatched Tcm is induced under a very safe procedure involving conditioning with sub-lethal 5.5 Gy TBI and autologous BMT.

Example 2

MHC Mismatched Tcm Survive in Host Mice in the Absence of a Bone Marrow Transplant In light of the above data, the ability of the Tcm cells alone to induce tolerance in the absence of BM was assessed. The outreach of such a protocol would be far greater. Specifically, induction of immune tolerance through administration of anti-$3^{rd}$-party Tcm cells alone, under safe conditioning, would be an asset not only for immune compromised individuals, but could possibly allow for the treatment of non-malignant hematological diseases (e.g. anemia & thalassemia), autoimmune diseases and could provide a platform for cell therapy administration. Initially the present inventors attempted to define the minimal irradiation dose under which Tcm cells of F1 origin engraft, in order to set up the model in which tolerance induction in hosts can be tested. To this end, Balb/c mice were exposed to a range of sublethal conditioning doses with and without adoptive transfer of CB6 F1-Tcm cells. Analysis of whole peripheral blood for $H2^{db}$-positive Tcm cells showed that the minimal irradiation dose under which Tcm could be detected (i.e. where Tcm cells were not rejected) was 5.5 Gy TBI (FIG. 5). Consequently, sustainability of fully allogeneic C57BL/6 derived Tcm to survive under a sublethal TBI dose of 5.5 Gy was tested (as depicted in FIG. 1C). This experiment was intended to verify that cells of allogeneic origin do not induce GVHD and that the deletion of anti-donor T cells is not mediated through alloreactivity but rather by veto activity. Moreover, once translated to humans and in order to produce "off-the-shelf" tolerance inducing Tcm, cells will most probably be derived from allogeneic, non-matched, sources. Results showed that C57BL/6 derived allogeneic Tcm were able to survive within 5.5 Gy irradiated Balb/c hosts (as depicted in FIG. 1C), displaying slightly lower Tcm percentages in the peripheral blood than those in mice receiving CB6 F1 Tcm (FIGS. 6A-B). This result may be attributed to a very slow rejection process of the Tcm cells. Although Tcm cells persist in the blood for well over a year, the reduction in their number over the first few months post injection, taken together with the elimination of anti-host clones detected in the chromium release assay, strongly suggests that the Tcm induce peripheral tolerance.

Therefore the application of Tcm-alone is used to create a window of opportunity, at least for few months, for administration of treatments, such as cell-therapy.

Example 3

MHC Mismatched Tcm Support Adoptive Transfer of Cells from the Same Donor

To test the hypothesis that Tcm cells can be used for adoptive cell therapy, the present inventors utilized a transgenic OT1 mice that carries a TCR against the ovalbumin peptide. The motivation to use OT1 transgenic cells in this context stemmed from the idea that these cells can be used as a model for cell-therapies known as donor lymphocyte infusion (DLI) with the whole population of donor T cells or with antigen specific T cells directed against viral or tumor antigens.

Initially, naïve $CD8^+OT1^+CD45.1^+$ T cells were infused into the Tcm chimeric mice, 90 days post initial adoptive transfer of the Tcm. The main goal was to define whether the surviving Tcm population can facilitate engraftment of newly infused allogeneic cells. Prior to injection of naïve Tg cells the Tcm population in chimeric mice were analyzed by FACS. Thus, 2/5 and 9/11 mice that had received C57BL/6 Tcm or CB6-Tcm, respectively, maintained their Tcm population (FIGS. 6A-B).

These mice were further conditioned on day 90 post-transplantation with 2 Gy TBI (in order to deplete some T cells to allow for the new T cells to be introduced) and the mice were then infused with $2 \times 10^6$ OT1 cells ($H-2^b$). Interestingly, when evaluated on day 120 (30 days post OT1 cell transplantation) the OT1 cells could be detected only in those mice that had displayed a Tcm population prior to transplantation (FIG. 7). These preliminary results, showing that in mice displaying a population of Tcm addition of cells from the same donor origin can be accepted, were further substantiated using transgenic OT-1 cells, as follows: CD8+ OT-1 cells were transplanted along with the Tcm on day 0, to prevent the need for secondary conditioning (2 Gy TBI previously employed on day 90), and the presence of OT1 cells in the peripheral blood was monitored at different time points after cell infusion.

As shown in FIG. 8, the results of this experiment illustrate that:

1. C57BL/6 Tcm as well as (Balb×C57BL)F1 Tcm can persist in allogeneic recipients.
2. C57BL/6 Tcm can confer protection to CD8+OT-1 naïve cells bred on C57BL/6 background (OT-1+CD45.1+ RAG−) when co-injected, while OT-1 cells on their own fade away from circulation.
3. CB6(F1) Tcm that express the MHC haplotype of C57BL/6 ($H-2^b$) mice can also confer protection of OT-1 naïve cells.

Example 4

Anti-Third Party Tcm Veto Cells Prepared from Cells of OT-1 Mice Engraft and Survive In-Vivo Experiments were carried out in mice conditioned with reduced intensity conditioning (RIC), suitable for clinical implementation. Hence, 5.5 Gy TBI sublethally irradiated Balb/c mice, were injected with different concentrations of non-syngeneic Tcm cells from an OT-1 mouse origin (illustrated in FIG. 9). Tcm cells were present in peripheral blood of these mice at least for 30 days. Thus, the survival of MHC mismatched Tcm cells is induced under a safe RIC procedure.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated cell having a central memory T-lymphocyte (Tcm) phenotype, said cell being a non-graft versus host (GVHD)-inducing anti-third party cell, being tolerance-inducing and capable of homing to the lymph nodes following transplantation, said cell being transduced to express a cell surface receptor, said cell surface receptor comprising a T cell receptor signaling module and an extracellular domain directed against a disease antigen.

2. An isolated cell having a central memory T-lymphocyte (Tcm) phenotype, said cell being a non-graft versus host (GVHD)-inducing anti-third party cell, being tolerance-inducing and capable of homing to the lymph nodes following transplantation, said cell being transduced to express a chimeric antigen receptor (CAR) comprising an extracellular domain directed against a disease antigen.

3. An isolated cell having a central memory T-lymphocyte (Tcm) phenotype, said cell being a non-graft versus host (GVHD)-inducing anti-third party cell, being tolerance-inducing and capable of homing to the lymph nodes following transplantation, said cell being transduced to express a chimeric antigen receptor (CAR), wherein said CAR comprises a co-stimulatory domain and comprises an extracellular domain directed against a disease antigen.

4. The isolated cell of claim 1, wherein said cell surface receptor comprises a transgenic T cell receptor (tg-TCR) or a chimeric antigen receptor (CAR).

5. The isolated cell of claim 2, wherein said CAR comprises:
   an antigen binding domain being an antibody or an antigen-binding fragment; or
   a CD3ζ; or
   at least one co-stimulatory domain selected from the group consisting of CD28, CD134/OX40, CD137/4-1BB, Lck, ICOS and DAP10; or at least two co-stimulatory domains selected from the group consisting of CD28, CD134/OX40, CD137/4-1BB, Lck, ICOS and DAP10.

6. The isolated cell of claim 5, wherein the antigen-binding fragment is a Fab or a scFv.

7. The isolated cell of claim 1, wherein said disease antigen is selected from the group consisting of a tumor antigen, a viral antigen, a bacterial antigen, a fungal antigen, a protozoa antigen, and a parasite antigen.

8. The isolated cell of claim 7, wherein:
said tumor antigen is associated with a solid tumor; or
said tumor antigen is associated with a hematologic malignancy; or
said tumor antigen is selected from the group consisting of CD19, CD20, CD22, ROR1, mesothelin, CD33/IL3Ra, c-Met, PSMA, Glycolipid F77, EGFRvIII, Her2, GD2, gp100, p53, carcinoembryonic antigen (CEA), MART-1, Telomerase reverse transcriptase (TERT), Claudin-6, Receptor tyrosine-protein kinase extracellular domain (ErbB2-ECD), Receptor tyrosine-protein kinase intracellular domain (ErbB2-ICD), Histone H1.2, Histone H4, Tyrosinase, alphafetoprotein (AFP), MAGE A3, AIM-2a, AFP, ART-4, CLCA2, Cyp-B, EphA2, hTERT, iCE, FGF-5, G250, GnT-V, HST-2 (FGF-6), Livin (ML-IAP), MUC1, MUC2, PRAME, PSMA, P15, RAGE, RU1, RU2, SART-1, SART-3, SART-2, SOX10, Survivin, Survivin-2Bg, TRG, Neo-PAP, CAMEL and NY-ESO-1; or
said viral antigen is of a virus selected from the group consisting of human immunodeficiency virus (HIV), T-cell leukemia virus type 1 (TAX), influenza virus, herpes virus, papilloma virus, hepatitis viruses, ebola virus, human T-lymphotropic virus (HTLV), rubella virus, measles virus, rabies virus, lymphocytic choriomeningitis (LCM), rotavirus, mumps virus, adenovirus, BK polyomavirus (BKV), and Epstein-Barr virus (EBV).

9. The isolated cell of claim 1, wherein said cell is further genetically modified to repress expression of at least one endogenous immunological checkpoint gene in said cell.

10. The isolated cell of claim 9, wherein said immunological checkpoint gene is selected from the group consisting of a PD or CTLA gene.

11. The isolated cell of claim 1, wherein said Tcm phenotype comprise a $CD3^+$, $CD8^+$, $CD62L^+$, $CD45RA^-$, $CD45RO^+$ signature, and optionally wherein at least 50% of the isolated cells are CD3+CD8+ cells of which at least 50% have said signature.

12. A population of cells comprising the isolated cell of claim 1.

13. A pharmaceutical composition comprising the population of cells of claim 12 and a pharmaceutically active carrier.

14. The isolated cell of claim 1, wherein said non-graft versus host (GVHD)-inducing anti-third party cell, being tolerance-inducing and capable of homing to the lymph nodes following transplantation, is generated by a method comprising:
(a) contacting peripheral blood mononuclear cells (PBMC) with a third party antigen or antigens in the presence of IL-21 so as to allow enrichment of antigen reactive cells; and
(b) culturing said cells resulting from step (a) in the presence of IL-21, IL-15 and IL-7 so as to allow proliferation of anti-third party cells comprising said central memory T-lymphocyte (Tcm) phenotype.

15. The isolated cell of claim 14, wherein said method further comprises depleting CD4+ and/or CD56+ cells prior to step (a).

* * * * *